(12) United States Patent
Takeuchi et al.

(10) Patent No.: US 6,184,386 B1
(45) Date of Patent: Feb. 6, 2001

(54) COMPOUND FOR PHOTOGRAPHY

(75) Inventors: Hiroshi Takeuchi; Shinichi Ichikawa; Keisuke Matsumoto, all of Kanagawa (JP)

(73) Assignee: Fuji Photo Film Co., Ltd., Kanagawa (JP)

( * ) Notice: Under 35 U.S.C. 154(b), the term of this patent shall be extended for 0 days.

(21) Appl. No.: 09/140,835

(22) Filed: Aug. 26, 1998

(30) Foreign Application Priority Data

Sep. 2, 1997 (JP) .................................................. 9-237513
Mar. 9, 1998 (JP) ................................................. 10-057172

(51) Int. Cl.$^7$ .................................................. C07D 277/36

(52) U.S. Cl. ........................................... 548/187; 548/188

(58) Field of Search ..................................... 548/188, 187

(56) References Cited

U.S. PATENT DOCUMENTS 3,004,033 * 10/1961 D'amico ................................ 548/188
5,380,633    1/1995 Harder et al. .

OTHER PUBLICATIONS

Palla, Ann. Technol. Agric. 23(3) 367 Abstract Only, 1974.*

* cited by examiner

*Primary Examiner*—Robert Gerstl
(74) *Attorney, Agent, or Firm*—Sughrue, Mion, Zinn, Macpeak & Seas, PLLC

(57) ABSTRACT

A compound for photography is described, which is represented by following formula (I):

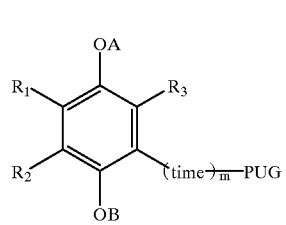

(I)

wherein $R_1$, $R_2$, and $R_3$ each represents a hydrogen atom or a group capable of being substituted; A and B each represents a hydrogen atom or a group which can be removed with an alkali; "time" represents a group releasing PUG after released from an oxidation product of the hydroquinone mother nucleus; m represents 0 or 1; and PUG represents a group represented by following formula (II):

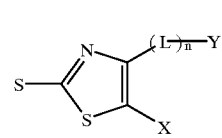

(II)

wherein X represents a hydrogen atom, an alkyl group, a carboxyl group, an alkoxycarbonyl group, a cyano group, or a carbamoyl group; Y represents a hydrogen atom, an alkyl group, an aryl group, a heterocyclic group, a carbamoyl group, or an alkoxycarbonyl group; L represents an alkylene group or an arylene group; and n represents 0 or 1.

4 Claims, No Drawings

COMPOUND FOR PHOTOGRAPHY

FIELD OF THE INVENTION

The present invention relates to a novel compound for photography oxidatively releasing a development inhibitor in a development process, and more particularly to a compound for a silver halide color photographic material having an improved interimage effect and an improved sharpness.

BACKGROUND OF THE INVENTION

It is known that by color developing a silver halide color photographic material, dyes such as indophenol, indoaniline, indamine, azomethine, phenoxazin, phenazine, and dyes similar to the above-described dyes are formed by the reaction of an oxidized aromatic primary amino color developing agent and couplers to form color images. In the system, for the color reproduction, a subtractive color process is usually used and for the process, silver halide emulsions selectively having sensitivities to blue, green and red respectively and color image-forming agents of yellow, magenta, and cyan each of which is in a complementary color relation with each of the above-described silver halide emulsions are used. That is, to form yellow color images, for example, acylacetanilide series or dibenzoylmethane series couplers are used, to form magenta color images, for example, pyrazolone series, pyrazolotriazole series, pyrazolobenzimidazole series, pyrazolopyrazole series, cyanoacetophnenone series, or indazolone series couplers are mainly used, and to form cyan color images, for example, phenol series or naphthol series couplers are used.

Now, each of the dyes formed from these couplers does not have an ideal absorption spectrum, in particular, the magenta and cyan dyes each has a broad absorption spectrum and/or has a side absorption in a short wavelength region, which are undesirable for color reproduction of color photographic materials. In particular, the side absorption in a short wavelength region has a tendency of lowering the saturation. As one means for improving the fault, it can be improved to some extent by causing an interimage effect.

The interimage effect is described, for example, in Hanson et al, *Journal of the Optical Society of America*, Vol. 42, pages 663 to 669 and A. Theils, *Zeitschrift fur Wissenschftliche Photographie, Photophysigue und Photochemie*, Vol. 47, pages 106 to 118 and pages 246 to 255.

It is described in U.S. Pat. Nos. 3,536,386 and 3,536,487 and JP-B-48-34169 (the term "JP-B" as used herein means an "examined Japanese patent publication") that the interimage effect is obtained by using 4-thiazoline-2-thione compounds.

However, when each of these compounds is mixed with a silver halide emulsion for coating, after preparing the coating composition containing them, the compound causes a bad action with the passage of time and also when the silver halide light-sensitive material is used after storing the light-sensitive material for a long period of time, there occurs a problem of lowering the sensitivity, etc. When the compound is added to a layer containing substantially no silver halide emulsion adjacent to a silver halide emulsion layer, the above-described problem cannot be avoided.

On the other hand, a means of releasing a compound of emphasizing the interimage effect by the oxidation during the development process by using a DIR hydroquinone is described in U.S. Pat. Nos. 3,379,529, 3,620,746, 4,377,634, and 4,332,878 and JP-A-6-308689 (the term "JP-A" as used herein means an "unexamined published Japanese patent application"). By these means, the occurrence of the above-described bad action after preparing the coating solution and the problem of causing lowering of the sensitivity after storing the light-sensitive material for a long period of time, which material is prepared by coating the coating solution are reduced and the interimage effect is obtained but these improvements are yet insufficient.

SUMMARY OF THE INVENTION

Accordingly, an object of the present invention is to provide a compound for photography for offering a silver halide color photographic material giving an excellent sharpness without reducing other photographic properties.

It has now been discovered that the above-described object can be achieved by the present invention described hereinbelow.

That is, according to a 1st aspect of the present invention, there is provided a compound for photography represented by following formula (I):

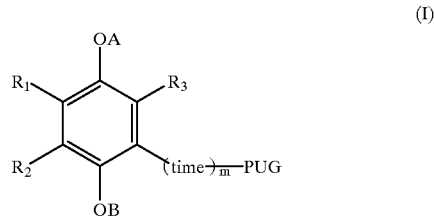

wherein $R_1$, $R_2$, and $R_3$ each represents a hydrogen atom or a group capable of being substituted; A and B each represents a hydrogen atom or a group which can be removed with an alkali; "time" represents a group which releases PUG after released from an oxidation product of the hydroquinone mother nucleus; m represents 0 or 1; and PUG represents a group represented by following formula (II):

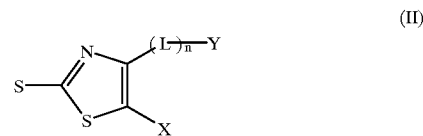

wherein X represents a hydrogen atom, an alkyl group, a carboxyl group, an alkoxycarbonyl group, a cyano group, or a carbamoyl group; Y represents a hydrogen atom, an alkyl group, an aryl group, a heterocyclic group, a carbamoyl group, or an alkoxycarbonyl group; L represents an alkylene group or an arylene group; and n represents 0 or 1.

According to a 2nd aspect of the present invention, there is provided the compound for photography of the 1st aspect wherein in the formula (II) described above, n represents 1; L represents a methylene group, an ethylene group, or a propylene group; Y represents a hydrogen atom, a carbamoyl group, or an alkoxycarbonyl group; and X represents a hydrogen atom, a methyl group, an ethyl group, a carboxyl group, an alkoxycarbonyl group, a cyano group, or a carbamoyl group.

Also, according to a 3rd aspect of the present invention, there is provided the compound for photography of the 1st aspect wherein in the formula (I) described above, $R_1$ represents an alkyl group, an alkylthio group, an acylamino group, or a ureido group.

Furthermore, according to a 4th aspect of the present invention, there is provided the compound for photography of the 1st aspect wherein in the formula (I), $R_1$ represents an alkylthio group, an acylamino group, or a ureido group and in the formula (II), n represents 1; L represents a methylene group; Y represents a hydrogen atom, a carbamoyl group, or an alkoxycarbonyl group; and X represents a hydrogen atom.

Further, according to a 5th aspect of the present invention, there is provided the-compound for photography of the 4th aspect wherein in the formula (II) described above, Y represents a carbamoyl group.

Furthermore, according to a 6th aspect of the present invention, there is provided the compound for photography of the 4th aspect wherein in the formula (II) described above, Y represents —C(=O)NHCH$_3$, —C(=O)NHC$_2$H$_5$, —C(=O)NHC$_3$H$_7$, or —C(=O)NHCH(CH$_3$)$_2$.

The novel compound (additive) for photography of the present invention can provide a silver halide color photographic material giving an excellent sharpness without reducing other photographic properties by being added preferably to a color photographic light-sensitive material, and more preferably to a color reversal photographic light-sensitive material.

DETAILED DESCRIPTION OF THE INVENTION

The present invention is described in detail below.

First, the compound represented by the formula (I) described above is explained in detail.

In the formula (I), $R_1$, $R_2$, and $R_3$ each represents a hydrogen atom or a group capable of being substituted. Examples of the group capable of being substituted include a halogen atom (e.g., fluorine atom, chlorine atom, chlorine atom, bromine atom, and iodine atom), a cyano group, a nitro group, an ammonio group (e.g., trimethylammonio), a phosphonio group, a sulfo group, a sulfino group, a carboxyl group, a phosphpono group, a hydroxy group, a mercapto group, a hydrazino group, an alkyl group (e.g., methyl, ethyl, n-propyl, isopropyl, t-butyl, n-octyl, cyclopentyl, and cyclohexyl), an alkenyl group (e.g., allyl, 2-butenyl, and 3-pentenyl), an alkinyl group (e.g., propargyl and 3-penthinyl), an aralkyl group (e.g., benzyl and phenetyl), an aryl group (e.g., phenyl, naphthyl, and 4-methylphenyl), a heterocyclic group (e.g., pyridyl, furyl, imidazolyl, piperidyl, and morpholino), an alkoxy group (e.g., methoxy, ethoxy, and butyloxy), an aryloxy group (e.g., phenoxy and 2-naphthyloxy), an alkylthio group (e.g., methylthio and ethylthio), an arylthio group (e.g., phenylthio), an amino group (e.g., an unsubstituted amino, methylamino, dimethylamino, ethylamino, and anilino), an acyl group (e.g., acetyl, benzoyl, formyl, and pivaloyl), an alkoxycarbonyl group (e.g., methoxycarbonyl and ethoxycarbonyl), an aryloxycarbonyl group (e.g. phenoxycarbonyl), a carbamoyl group (e.g., unsubstituted carbamoyl, N,N-dimethylcarbamoyl, N-ethylcarbamoyl, and N-phenylcarbamoyl), an acyloxy group (e.g., acetoxy and benzoyloxy), an acylamino group (e.g., acetylamino and benzoylamino), an alkoxycarbonylamino group (e.g., methoxycarbonylamino), an aryloxycarbonylamino group (e.g., phenoxycarbonylamino), a ureido group (e.g., unsubstituted ureido, N-methylureido, and N-phenylureido), a sulfonamido group (e.g., methanesulfonamido and benzenesulfonamido), an alkylsulfonyloxy group (e.g., methylsulfonyloxy), an arylsulfonyloxy group (e.g., phenylsulfonyloxy), an alkylsulfonyl group (e.g., mesyl), an arylsulfonyl group (e.g., tosyl), an alkoxysulfonyl group (e.g., methoxysulfonyl), an aryloxysulfonyl group (e.g., phenoxysulfonyl), a sulfamoyl group (e.g., unsubstituted sulfamoyl, N-methylsulfamoyl, N,N-dimethylsulfamoyl, and Nphenylsulfamoyl), an alkylsulfinyl group (e.g., methylsulfinyl), an arylsulfinyl group (e.g., phenylsulfinyl), an alkoxysulfinyl group (e.g., methoxysulfinyl), an aryloxysulfinyl group (e.g., phenoxysulfinyl), and a phosphoric acid amido group (e.g., N,N-diethylphosphotic acid amido). These groups may be further substituted with the same group as that of $R_1$, $R_2$, or $R_3$. Also, when 2 or more substituents exist, they may be the same or different. Furthermore, $R_1$ and $R_2$ may combine to form a ring.

$R_1$, $R_2$, and $R_3$ each is preferably a hydrogen atom, an alkyl group having from 1 to 30 carbon atoms, an aryl group having from 6 to 30 carbon atoms, an alkoxy group having from 1 to 30 group, an aryloxy group having from 6 to 30 carbon atoms, an alkylthio group having from 1 to 30 carbon atoms, an arylthio group having from 6 to 30 carbon atoms, an acylamino group having from 1 to 30 carbon atoms, a ureido group having from 1 to 30 carbon atoms, a sulfonamido group having from 1 to 30 carbon atoms, or a halogen atom, and is more preferably a hydrogen atom, an alkyl group having from 1 to 25 carbon atoms, an aryl group having from 6 to 25 carbon atoms, an alkylthio group having from 1 to 25 carbon atoms, an arylthio group having from 6 to 25 carbon atoms, an acylamino group having from 1 to 25 carbon atoms, a ureido group having from 1 to 25 carbon atoms, or a sulfonamido group having from 1 to 25 carbon atoms.

In the formula (I), A and B each represents a hydrogen atom or a group which can be removed with an alkali. The group shown by A or B, which can be removed with an alkali, preferably includes groups which can be hydrolyzed, such as an acyl group, an alkoxycarbonyl group, a carbamoyl group, an imidoyl group, an oxazolyl group, a sulfonyl group, etc.; the precursor group of the type utilizing the reverse Michael reaction described in U.S. Pat. No. 4,009,029; the precursor group of the type of utilizing the anion generated after a ring cleaving reaction as an intramolecular nucleophilic group described in U.S. Pat. No. 4,310,612; the precursor group that an anion causes an electron transfer via a conjugated system, whereby a cleavage reaction is caused described in U.S. Pat. Nos. 3,674,478, 3,932,480, and 3,993,661; the precursor group of causing a cleavage reaction by the electron transfer of an anion reacted after ring cleaving reaction described in U.S. Pat. No. 4,335,200; and the precursor group utilizing an imidomethyl group described in U.S. Pat. Nos. 4,363,865 and 4,410,618. A and B are more preferably a hydrogen atom.

In the formula (I), "time" represents a divalent group which is released as —(time)$_m$—PUG with a nucleophilic agent (such as, an hydroxide ion, a sulfite ion, hydroxylamine, etc.) when the hydroquinone mother nucleus becomes a quinone compound by being oxidized with the oxidation product of a developing agent during development processing and thereafter can release PUG, and may have a timing control function. The case were m is 0 means that PUG is directly bonded to the hydroquinone mother nucleus. When "time" is a divalent linkage group having a timing control function, the group shown by "time" practically represents the same group as the time group explained on and after page 5 of JP-A-4-151144. In addition, m is preferably 0.

Then, the above-described formula (II) showing PUG is explained.

In the formula (II), X represents a hydrogen atom, an alkyl group, a carboxyl group, an alkoxycarbonyl group, a cyano group, or a carbamoyl group; Y represents a hydrogen atom, an alkyl group, an aryl group, a heterocyclic group, a carbamoyl group, or an alkoxycarbonyl group; L represents an alkylene group or an arylene group; and n represents 0 or 1 as described above.

The groups shown by X, Y, and L except a hydrogen atom may be substituted and as the substituents, there are groups described above as the groups capable of being substituted shown by $R_1$, $R_2$, and $R_3$ of the formula (I).

In the formula (II), X is preferably a hydrogen atom, an alkyl group having from 1 to 10 carbon atoms, a carboxyl group, an alkoxycarbonyl group having from 2 to 20 carbon atoms, a cyano group, or a carbamoyl group having from 1 to 20 carbon atoms, and is more preferably a hydrogen atom, an alkyl group having from 1 to 8 carbon atoms, a carboxyl group, an alkoxycarbonyl group having from 2 to 15 carbon atoms, a cyano group, or a carbamoyl group having from 1 to 15 carbon atoms.

In the formula (II), Y is preferably a hydrogen atom, an alkyl group having from 1 to 10 carbon atoms, an aryl group having from 6 to 10 carbon atoms, a heterocyclic group, a carbamoyl group having from 1 to 20 carbon atoms, or an alkoxycarbonyl group having from 2 to 20 carbon atoms, and is more preferably a hydrogen atom, a carbamoyl group having from 1 to 15 carbon atoms, or an alkoxycarbonyl group having from 2 to 15 carbon atoms.

Also, in the formula (II), L is preferably an alkylene group having from 1 to 10 carbon atoms or an arylene group having from 6 to 10 carbon atoms and is more preferably an alkylene group having from 1 to 8 carbon atoms.

As the preferred combinations of X, Y and L, X is a hydrogen atom, L is a methylene group, and Y is a carbamoyl group selected from an N-methylcarbamoyl group, an N-ethylcarbamoyl group, an N-propylcarbamoyl group and an Nisopropylcarbamoyl group.

Then, practical examples of the compound represented by the formula (I) used in the present invention are shown below but the compounds in the present invention are not limited to these compounds.

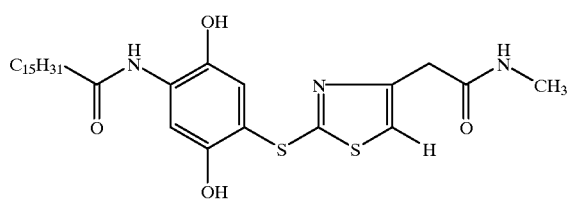

I-1

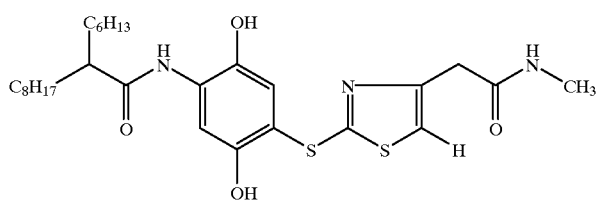

I-2

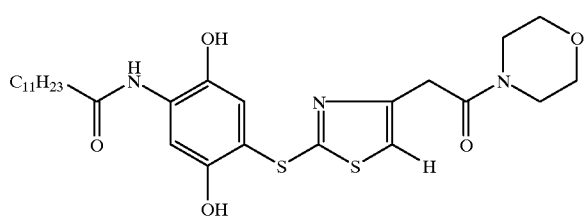

I-3

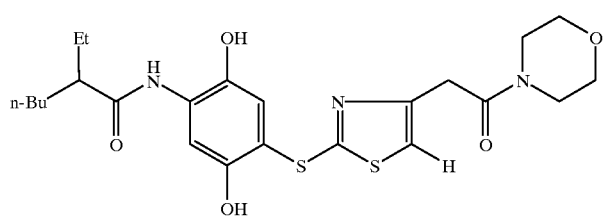

I-4

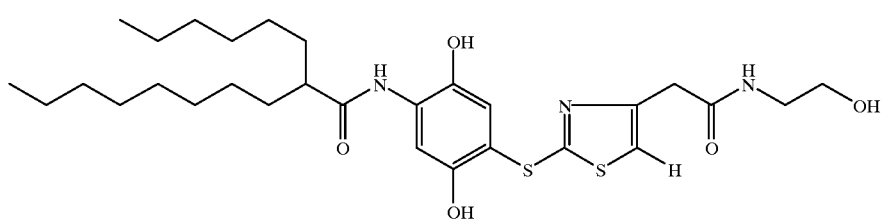

I-5

I-6
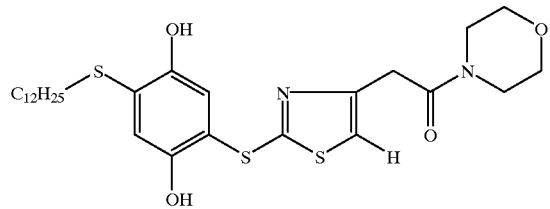
I-7
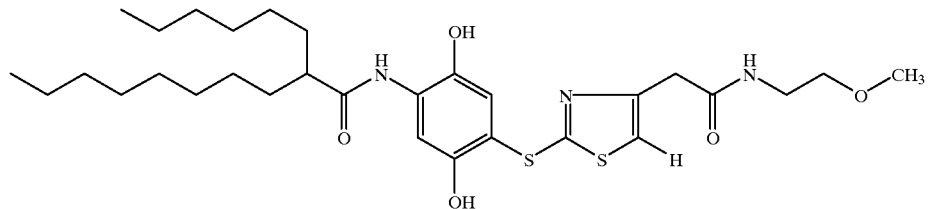
I-8
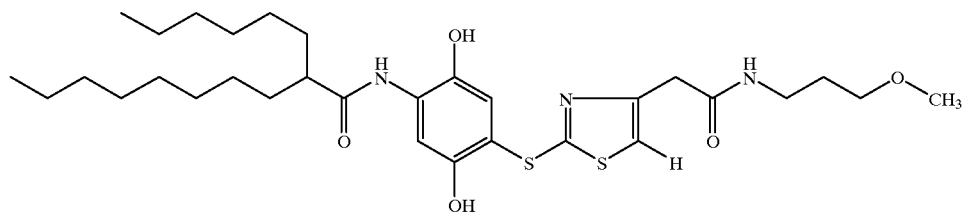
I-9
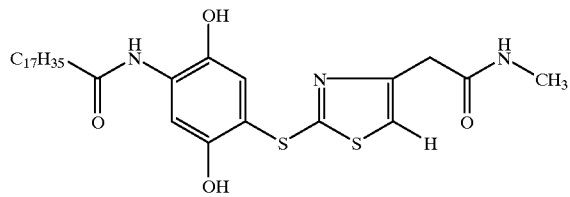
I-10
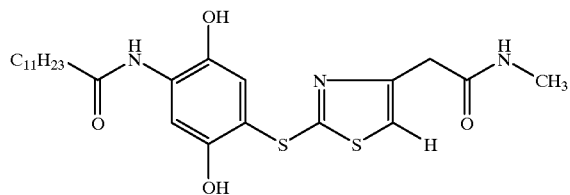
I-11
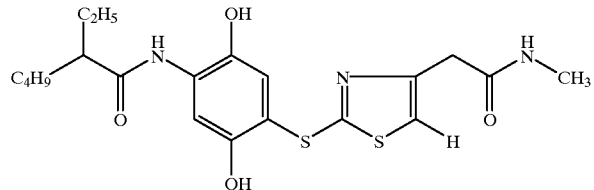
I-12
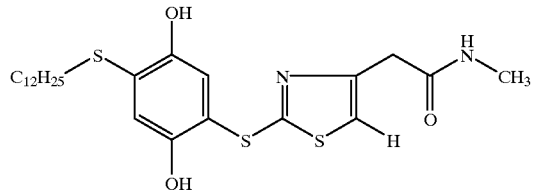

-continued
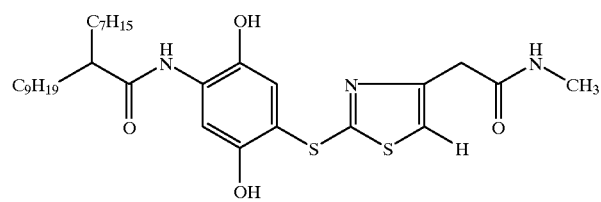
I-13
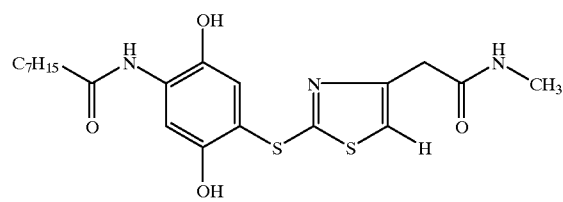
I-14
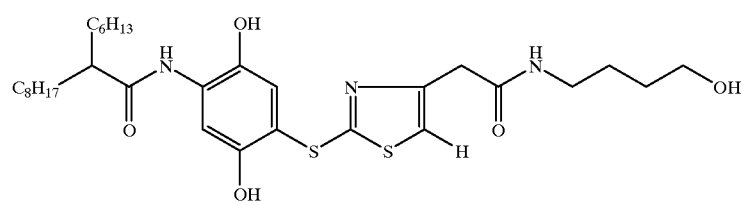
I-15
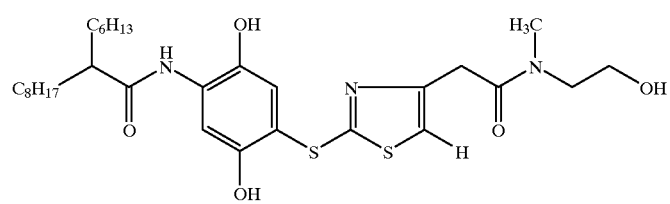
I-16
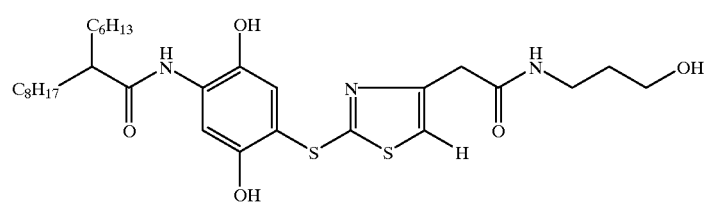
I-17
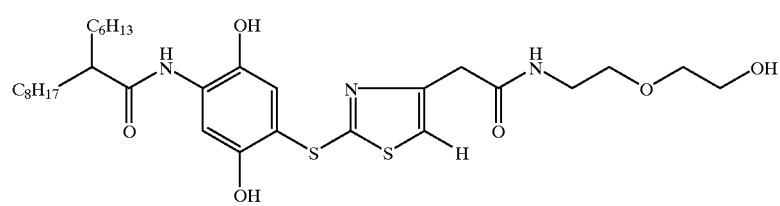
I-18
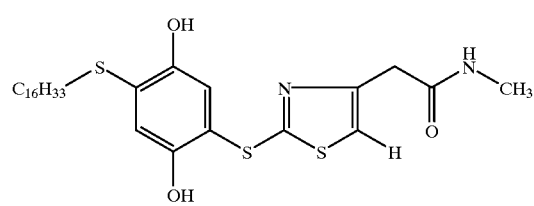
I-19

I-20
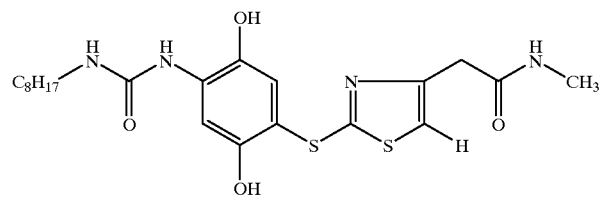
I-21
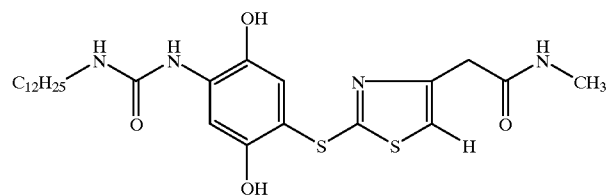
I-22
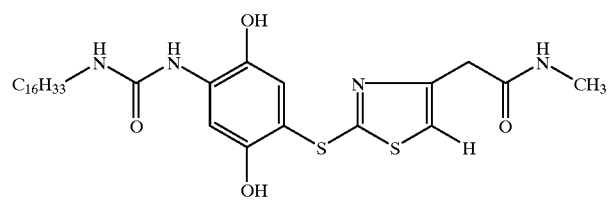
I-23
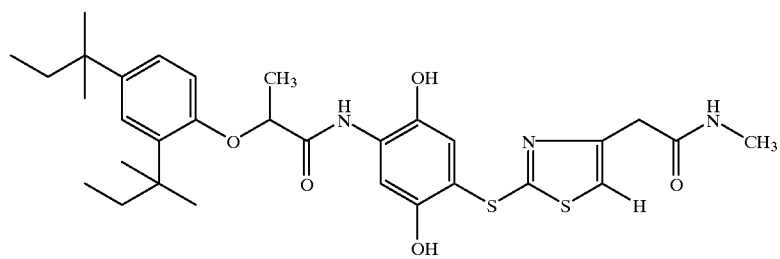
I-24
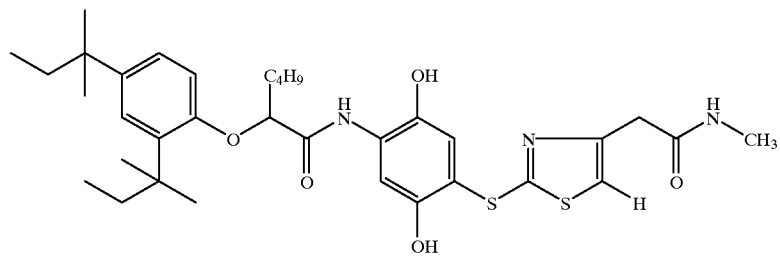
I-25
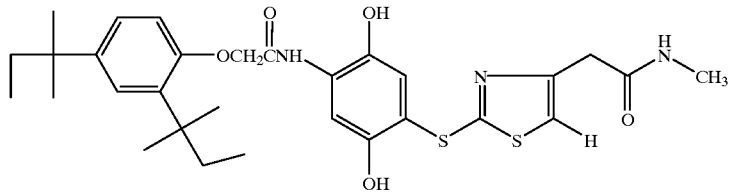
I-26
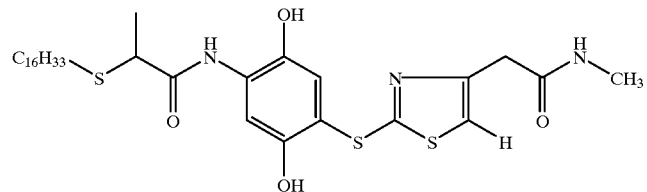

I-27
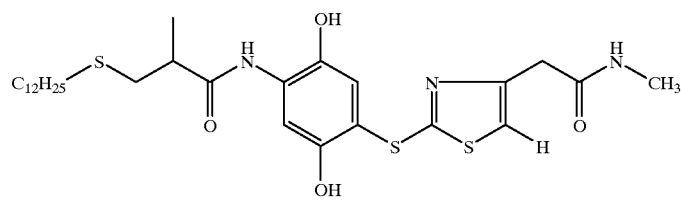
I-28
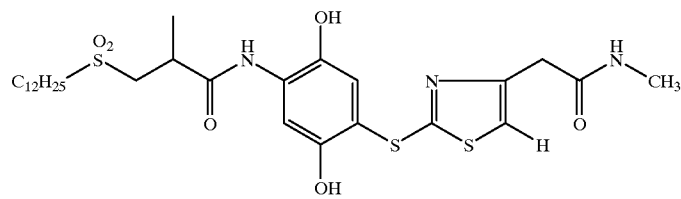
I-29
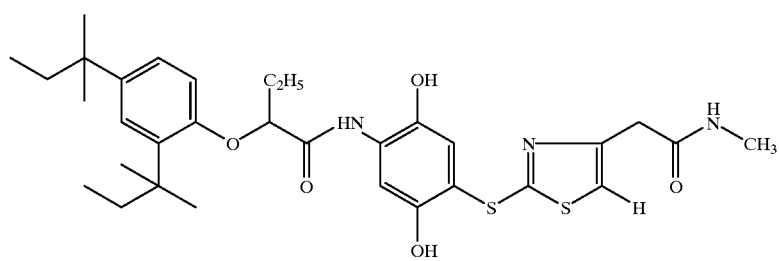
I-30
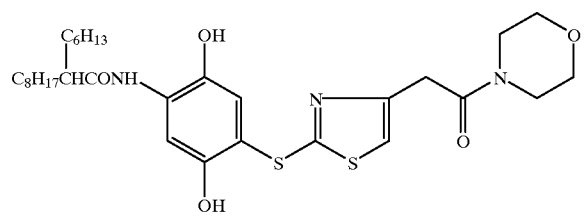
I-31
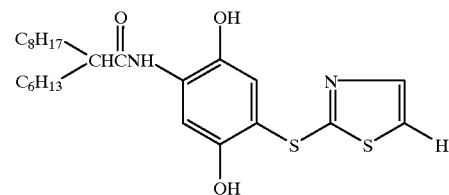
I-32
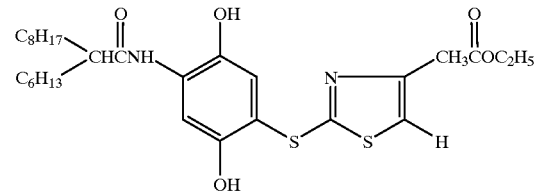
I-33
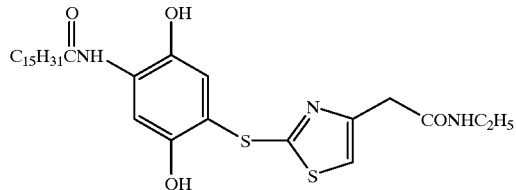

-continued
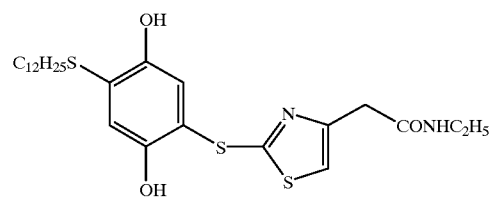
I-34
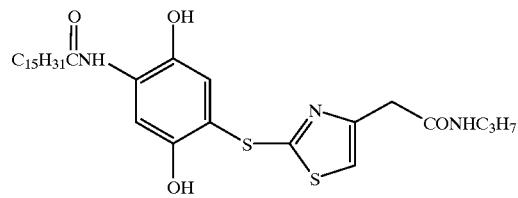
I-35
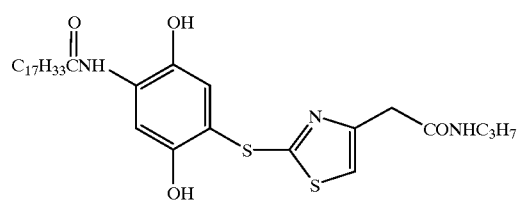
I-36
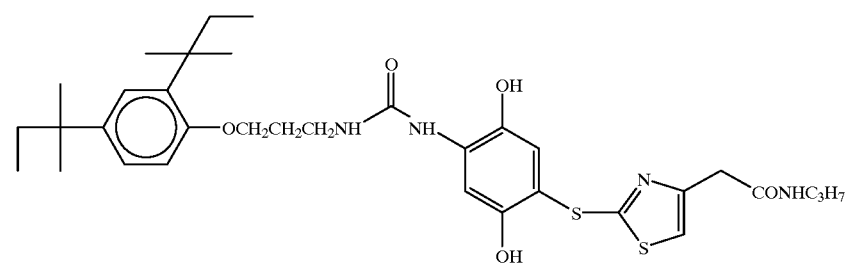
I-37
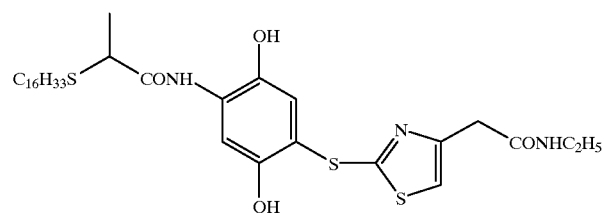
I-38
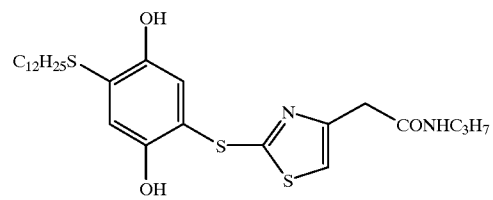
I-39
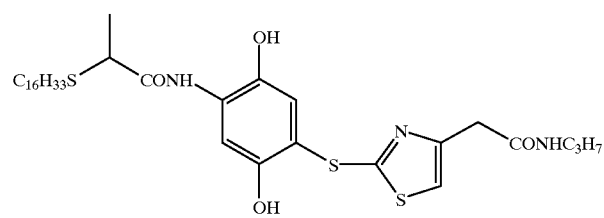
I-40

-continued

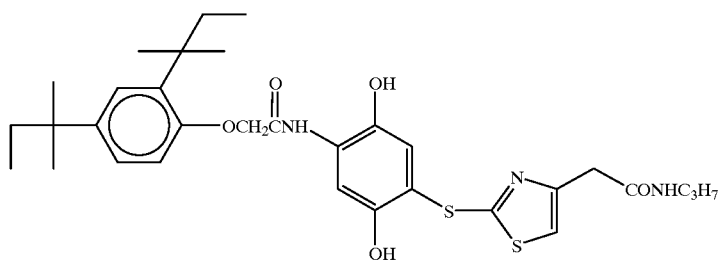
I-41

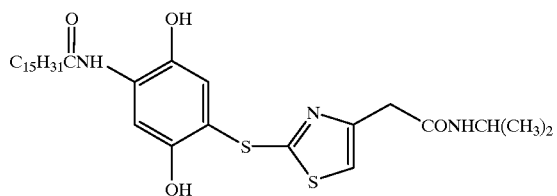
I-42

The compounds shown by the formula (I) can be synthesized according to the methods described in JP-A-3-226744, JP-A-3-226745, JP-A-238346, JP-A-4-238347, etc. Also, PUG shown by the formula (II), which is released from the compound of the formula (I), can be synthesized according to the methods described, for example, in Weissberger et al., *The Chemistry of Heterocyclic Compounds*, Vol. 34, No. 2, pages 369 to 560; Schaumann et al., *Methoden der Oraanishcen Chemie*, Vol. E8b, pages 1 to 398; Katritzky et al., Comprehensive Heterocyclic Chemistry, Vol. 6, pages 235 to 332, etc.

Examples of the practical synthesis courses of the compounds in the present invention and synthesis examples thereof are shown below but the synthesis methods of the compounds in the present invention are not limited to them.

That is, the practical synthesis courses of the compounds of the formula (I) wherein $R_1$ is an alkylthio group, an acrylamino group, and a ureido group are shown below.

In addition, in each of the courses (1), (2) and (3), R is an alkyl group.

(1)

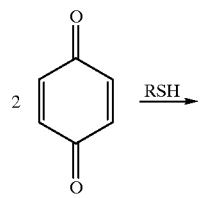

-continued

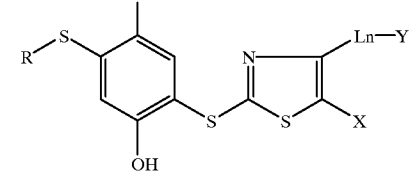

(2)

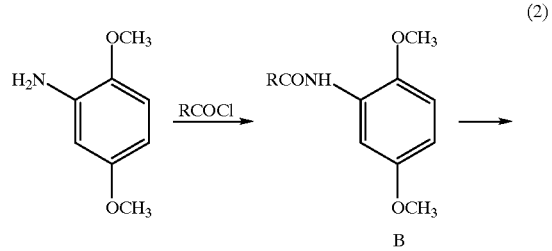

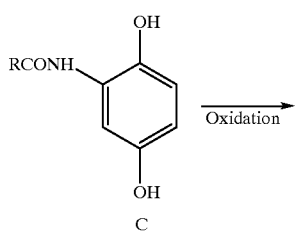

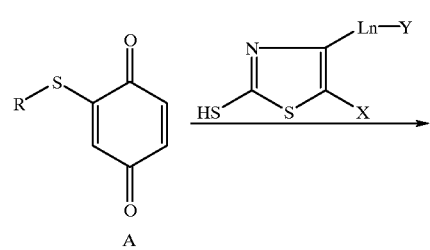

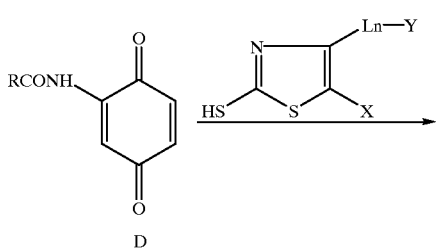

-continued

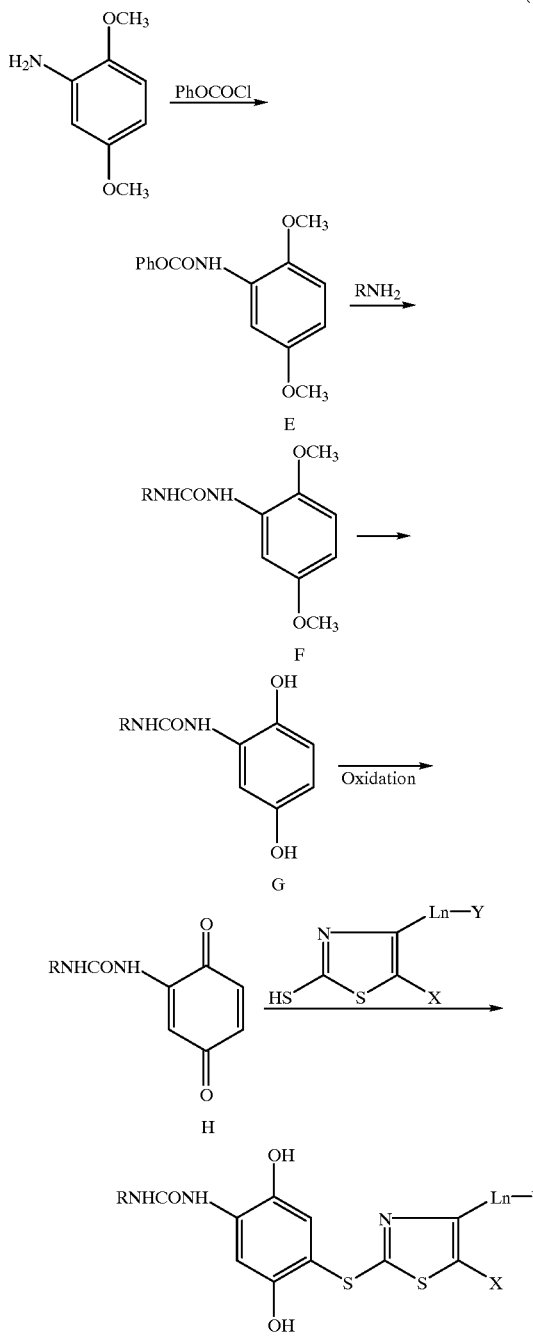

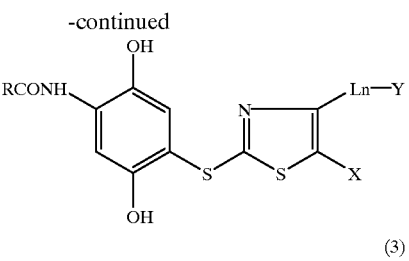

The amount of the compound of the present invention shown by the formula (I) differs depending upon the property and the purpose of the silver halide photographic material to which the compound is applied and the developing process but is generally preferably from $10^{-1}$ to $10^{-5}$ mol, and more preferably from $3\times10^{-2}$ to $3\times10^{-4}$ mol per mol of the silver halide existing in the same layer or in an adjacent layer.

To introduce the compound of the present invention shown by the formula (I) to the silver halide photographic material, it is preferred that after dissolving the compound in a high-boiling organic solvent, the solution is emulsified and dispersed in the presence of a surface active agent and the emulsified dispersion is added to a hydrophilic colloid, or that the compound is dispersed in a state of fine crystal or amorphous solid, and the dispersion is added to a hydrophilic colloid.

When the compound of the present invention is dissolved in the high-boiling organic solvent, other organic solvent, such as ethyl acetate, butyl acetate, methanol, ethanol, isopropanol, methyl ethyl ketone, cyclohexane, dimethyl formamide or dimethyl acetamide may be used together for the purpose of assisting the dissolution.

The high-boiling organic solvent which can be used together with the compound of the present invention may be either liquid or solid at ordinary temperature and may be any solvent usually used for a photographic light-sensitive material. Preferred examples of the high-boiling organic solvent include phosphates (for example, tricresyl phosphate, triphenyl phosphate, trihexyl phosphate, tricyclooctyl phosphate, tricyclopentyl phosphate, trioctyl phosphate, tricyclohexyl phosphate, tri-2-ethylhexyl phosphate, and tri3-methyl-5-dimethylhexyl phosphate), phthalates (for example, dibutyl phthalate, dicyclohexyl phthalate, di-2-ethylhexyl phthalate, dioctyl phthalate, and dihexyl phthalate), carboxamides (for example, N,N-diethyllaurylamide, N,Ndimethylpalmitoylamide, and N,N-dimethyloleylamide), with phosphates being particularly preferred.

The high-boiling organic solvent which can be used together with the compound of the present invention can preferably be used in a range from 0.1 to 100 times as much as the weight of the compound of the present invention, and it can particularly preferably be used in a range from 2 to 10 times as much as the weight of the compound of the present invention. A prularity of high-boiling organic solvent may be used together. Further, for the purpose of improving the stability of emulsified dispersion thus obtained, the compound of the present invention may be emulsified and dispersed in the presence of a compound known in the photographic field other than that of the present invention (for example, an ultraviolet absorbent, an image forming coupler, a color stain preventing agent, a water-insoluble polymer, and a discoloration preventing agent).

A color photographic light-sensitive material for which the compound for photography of the present invention is preferably used has on a support a red-sensitive silver halide emulsion layer, a green-sensitive silver halide emulsion layer, a blue-sensitive silver halide emulsion layer, and light-insensitive interlayer(s). At least one light-insensitive interlayer exists between light-sensitive layers and it is desirable that two interlayers exist. Further, it is preferred that each light-sensitive layer comprises at least three sub-layers having different sensitivity from one another.

Preferred practical examples of a silver halide color photographic material is shown below.

That is, from the support side;

Layer 1: Antihalation layer

Layer 2: Interlayer layer 3: Interlayer (containing colloidal silver or fogged fine-grain silver halide)

Layer 4: Low-sensitivity red-sensitive emulsion layer
Layer 5: Intermediate-sensitivity red-sensitive emulsion layer
Layer 6: High-sensitivity red-sensitive emulsion layer
Layer 7: Interlayer
Layer 8: Interlayer (containing colloidal silver or fogged fine-grain silver halide)
Layer 9: Low-sensitivity green-sensitive emulsion layer
Layer 10: Intermediate-sensitivity green-sensitive emulsion layer
Layer 11: High-sensitivity green-sensitive emulsion layer
Layer 12: Interlayer
Layer 13: Yellow filter layer
Layer 14: Low-sensitivity blue-sensitive emulsion layer
Layer 15: Intermediate-sensitivity blue-sensitive emulsion layer
Layer 16: High-sensitivity blue-sensitive emulsion layer
Layer 17: 1st protective layer
Layer 18: 2nd protective layer
Layer 19: 3rd protective layer When a light-sensitive layer is composed of at least three sub-layers having the same spectral sensitivity as one another but having a different sensitivity from one another, the ratio of the coated silver amount of each layer is preferably as follows. That is,-when the total silver amount of the same spectral sensitivity layers is 100%, the silver amount of the high-sensitivity emulsion layer is from 15 to 40%, that of the intermediate-sensitivity emulsion layer is from 20 to 50%, and that of the low-sensitivity emulsion layer is from 20 to 50%. In addition, it is preferred that the coated silver amount of the high-sensitivity emulsion layer is less than the coated silver amount of the intermediate-sensitivity emulsion layer or the low-sensitivity emulsion layer.

About silver halide photographic emulsions and various techniques and inorganic and organic materials which can be used for silver halide photographic materials containing the silver halide photographic emulsions, those described in *Research Disclosure* No. 308119 (December, 1989) can be generally used.

In addition to the above-described techniques and materials, more practically, the techniques and inorganic and organic materials which can be used for color photographic light-sensitive materials to which the silver halide emulsions can be applied are described in the following portions of EP-A-436938 and the patents cited below.

| | Items | Corresponding portions |
|---|---|---|
| 1) | Layer structure | Page 146, line 34 to page 147, line 25 |
| 2) | Silver halide emulsion | Page 147, line 26 to page 148, line 12 |
| 3) | Yellow coupler | Page 137, line 35 to page 146, line 33, page 149, lines 21 to 23 |
| 4) | Magenta coupler | Page 149, lines 24 to 28; page 3, line 5 to page 25, line 55 of EP-A-421453 |
| 5) | Cyan coupler | Page 149, lines 29 to 33; page 3, line 28 to page 40, line 2 of EP-A-432804 |
| 6) | Polymer coupler | Page 149, lines 34 to 38; page 113, line 39 to page 123, line 37 of EP-A-435334 |
| 7) | Colored coupler | Page 53, line 42 to page 137, line 34, page 149, lines 39 to 45 |
| 8) | Other functional coupler | Page 7, line 1 to page 53, line 41, page 149, line 46 to page 150, line 3; page 3, line 1 to page 29, line 50 of EP-A-435334 |
| 9) | Antiseptics and antifungal agent | Page 150, lines 25 to 28 |
| 10) | Formalin scavenger | Page 149, lines 15 to 17 |
| 11) | Other additives | Page 153, lines 38 to 47; page 75, line 21 to page 84, line 56, page 24, line 40 to page 37, line 40 of EP-A-421453 |
| 12) | Dispersion method | Page 150, lines 4 to 24 |
| 13) | Support | Page 150, lines 32 to 34 |
| 14) | Layer thickness, layer property | Page 150, lines 35 to 49 |
| 15) | Color development, black-and-white development, fogging step | Page 150, line 50 to page 151, line 47; page 34, lines 11 to 55, page 35, lines 14 to 22 of EP-A-442323 |
| 16) | Desilvering step | Page 151, line 48 to page 152, line 53 |
| 17) | Automatic processor | Page 152, line 54 to page 153, line 2 |
| 18) | Washing and stabilizing steps | Page 153, lines 3 to 37 |

The following examples are illustrated the present invention in more detail but not to limit the invention in any way.

EXAMPLE 1

(Synthesis methods of the compounds in the present invention)

Synthesis Example 1 (Synthesis of PUG (Compound K) of the Compound I-1)

To 180.0 g (1.63 mols) of ammonium dithiocarbamate was added 1.5 liters of isopropyl alcohol, the mixture was stirred and then 268.9 g (1.63 mols) of ethyl 4-chloro-3-oxobutanoate was added dropwise to the mixture. After stirring the resultant mixture for 3 hours under refluxing, 300 ml of water was added to the reaction mixture, the mixture was cooled to room temperature and crystals formed were collected by filtration under a reduced pressure to obtain crude crystals. The crude crystals were recrystallized from ethyl acetate to obtain 188 g (yield 57%) of 4-ethoxycarbonylmethyl-2-mercaptothiazole.

In 366 ml of water was suspended 185 g (0.91 mol) of 4-ethoxycarbonylmethyl-2-mercaptothiazole and 366 ml (1.84 mols) of an aqueous solution of 5 mol/l sodium hydroxide was added dropwise to the suspension. After heating the mixture for 2 hours in a steam bath with-stirring, the reaction mixture was cooled to room temperature, and 165 ml (1.90 mols) of concentrated hydrochloric acid was added dropwise to the mixture. The crystals formed were collected by filtration under a reduced pressure to provide 139.4 g (yield 87.4%) of 4-carboxymethyl-2-mercaptothiazole.

In 350 ml of tetrahydrofuran was dissolved 35 g (0.2 mol) of 4-carobxymethyl-2-mercaptothiazole and while cooling the solution to a temperature below 10° C., a solution made up of 41.3 g (0.2 mol) of N,N'-dicyclohexylcarbodiimide and 50 ml of tetrahydrofuran was added dropwise to the solution followed by stirring for one hour at room temperature. Then, while cooling the mixture to a temperature below 5° C., 15.5 g (0.2 mol) of a methanol solution of 40% N-methylamine was added dropwise to the mixture followed by stirring for 2 hours at room temperature. To the reaction mixture were added 750 ml of water and 500 ml of methanol followed by stirring and solids formed were removed by filtration. The filtrate was concentrated under a reduced pressure and purified by silica gel column chromatography to obtained 28.8 g (yield 76.5%) of the desired compound K (N-metylcarbamoylmethyl-2-mercaptothiazole) having a melting point of 146 to 148° C. The structure of the compound thus obtained was confirmed by various kinds of spectra and the elemental analysis.

Compound K (PUG of Compound I-1)

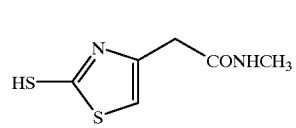

Synthesis Example 2 (Synthesis of Compound I-1)

In 650 ml of chloroform were dissolved 41.3 g (114 mmols) of 2-pentadecanoylamino-1,4-benzoquinone, 24 g (127 mmols) of Compound K, and 5 g (26 mmols) of p-toluenesulfonic acid monohydrate and the solution was stirred for 2 hours at 40° C. under a nitrogen gas atmosphere. The reaction mixture was concentrated under a reduced pressure and 300 ml of methanol was added to the residue formed followed by stirring. Crystals formed were collected by filtration under a reduced pressure to obtain 44.1 g (yield 70.4%) of the desired compound I-1 having a melting point of 135 to 137° C. The structure of the compound was confirmed by various kinds of spectra and the elemental analysis.

The properties of the compounds synthesized by the synthesis methods as in Synthesis Example 2 are shown in Tables 1, 2 and 3 below.

TABLE 1

| Compd. No. | Yield (%) | Melting Point (° C.) | Elemetal Analysis (%) Upper: Calculated Lower: Found |
|---|---|---|---|
| I-1 | 70 | 135–7 | C 61.17; H 7.88; N 7.64; S 11.66 |
|  |  |  | C 61.15; H 7.66; N 7.53; S 11.65 |
| I-2 | 68 | 106–8 | C 61.17; H 7.88; N 7.64; S 11.66 |
|  |  |  | C 61.16; H 7.78; N 7.55; S 11.68 |
| I-3 | 74 | 133–5 | C 58.99; H 7.15; N 7.64; S 11.66 |
|  |  |  | C 58.89; H 7.16; N 7.57; S 11.74 |
| I-4 | 78 | 177–9 | C 55.96; H 6.33; N 8.51; S 12.99 |
|  |  |  | C 55.87; H 6.44; N 8.32; S 12.87 |
| I-5 | 58 | Noncry. | C 60.07; H 7.82; N 7.25; S 11.06 |
|  |  |  | C 60.01; H 7.85; N 7.36; S 11.11 |
| I-6 | 78 | 92–4 | C 58.66; H 7.29; N 5.07; S 17.40 |
|  |  |  | C 58.56; H 7.22; N 5.10; S 17.42 |
| I-7 | 67 | 126–8 | C 60.68; H 7.98; N 7.08; S 10.80 |
|  |  |  | C 60.71; H 7.99; N 7.05; S 10.77 |
| I-8 | 65 | 104–6 | C 61.25; H 8.12; N 6.91; S 10.55 |
|  |  |  | C 61.21; H 8.10; N 6.89; S 10.55 |
| I-9 | 59 | 111–3 | C 62.36; H 8.20; N 7.27; S 11.10 |
|  |  |  | C 62.34; H 8.14; N 7.22; S 11.04 |
| I-10 | 86 | 137–8 | C 58.39; H 7.15; N 8.51; S 12.99 |
|  |  |  | C 58.34; H 7.12; N 8.44; S 12.87 |
| I-11 | 54 | Noncry. | C 54.90; H 6.22; N 9.60; S 14.65 |
|  |  |  | C 54.79; H 6.18; N 9.57; S 14.68 |
| I-12 | 63 | 85–7 | C 58.03; H 7.30; N 5.64; S 19.36 |
|  |  |  | C 58.01; H 7.18; N 5.56; S 19.34 |
| I-13 | 67 | Noncry. | C 62.36; H 8.20; N 7.27; S 11.10 |
|  |  |  | C 62.35; H 8.17; N 7.24; S 11.15 |
| I-14 | 75 | 177–9 | C 54.90; H 6.22; N 9.60; S 14.65 |
|  |  |  | C 54.78; H 6.15; N 9.55; S 14.68 |
| I-15 | 53 | Noncry. | C 61.25; H 8.12; N 6.91; S 10.55 |
|  |  |  | C 61.23; H 8.10; N 6.87; S 10.61 |
| I-16 | 57 | Noncry. | C 60.68; H 7.98; N 7.08; S 10.80 |
|  |  |  | C 60.58; H 7.82; N 7.05; S 10.84 |

TABLE 1-continued

| Compd. No. | Yield (%) | Melting Point (° C.) | Elemetal Analysis (%) Upper: Calculated Lower: Found |
|---|---|---|---|
| I-17 | 61 | Noncry. | C 60.68; H 7.98; N 7.08; S 10.80 |
|  |  |  | C 60.56; H 7.86; N 7.04; S 10.83 |

TABLE 2

| Compd. No. | Yield (%) | Melting Point | Elemental Analysis (%) Upper: Calculated Lower: Found |
|---|---|---|---|
| I-18 | 53 | Noncry. | C 59.68; H 7.92; N 6.74; S 10.28 |
|  |  |  | C 59.59; H 7.89; N 6.75; S 10.29 |
| I-19 | 74 | 88–90 | C 60.83; H 8.02; N 5.07; S 17.40 |
|  |  |  | C 60.76; H 8.00; N 5.05; S 17.50 |
| I-20 | 84 | 207–8 | C 54.06; H 6.48; N 12.01; S 13.74 |
|  |  |  | C 54.02; H 6.41; N 12.03; S 13.75 |
| I-21 | 81 | 172–3 | C 57.44; H 7.33; N 10.72; S 12.27 |
|  |  |  | C 57.35; H 7.28; N 10.68; S 12.25 |
| I-22 | 79 | 165–7 | C 60.18; H 8.01; N 9.68; S 11.08 |
|  |  |  | C 60.14; H 7.98; N 9.65; S 11.14 |
| I-23 | 82 | 187–9 | C 62.08; H 6.89; N 7.01; S 10.69 |
|  |  |  | C 62.04; H 6.79; N 7.02; S 10.72 |
| I-24 | 74 | 134–6 | C 63.62; H 7.38; N 6.55; S 9.99 |
|  |  |  | C 63.61; H 7.35; N 6.52; S 10.05 |
| I-25 | 82 | 185–7 | C 61.51; H 6.71; N 7.17; S 10.95 |
|  |  |  | C 61.49; H 6.68; N 7.15; S 10.98 |
| I-26 | 67 | 125–7 | C 59.68; H 7.92; N 6.73; S 15.42 |
|  |  |  | C 59.67; H 7.91; N 6.72; S 15.43 |
| I-27 | 68 | 121–3 | C 57.80; H 7.45; N 7.22; S 16.53 |
|  |  |  | C 57.75; H 7.44; N 7.18; S 16.55 |
| I-28 | 72 | 124–5 | C 54.79; H 7.06; N 6.85; S 15.67 |
|  |  |  | C 54.76; H 7.05; N 6.85; S 15.64 |
| I-29 | 81 | 97–99 | C 62.62; H 7.06; N 6.85; S 10.45 |
|  |  |  | C 62.63; H 7.10; N 6.86; S 10.46 |
| I-30 | 58 | Noncry. | C 61.46; H 7.82; N 6.94; S 10.58 |
|  |  |  | C 61.45; H 7.80; N 6.95; S 10.61 |
| I-31 | 63 | Noncry. | C 63.38; H 8.18; N 5.69; S 13.01 |
|  |  |  | C 63.29; H 8.11; N 5.68; S 13.21 |
| I-32 | 62 | Noncry. | C 61.67; H 7.85; N 4.96; S 11.35 |
|  |  |  | C 61.63; H 7.81; N 4.97; S 11.41 |

TABLE 3

| Compd. No. | Yield (%) | Melting Point (° C.) | Elemetal Analysis (%) Upper: Calculated Lower: Found |
|---|---|---|---|
| I-33 | 82 | 165–7 | C 61.78; H 8.04; N 7.45; S 11.37 |
|  |  |  | C 61.62; H 8.00; N 7.43; S 11.39 |
| I-34 | 81 | 84–6 | C 58.79; H 7.50; N 5.48; S 18.83 |
|  |  |  | C 58.75; H 7.46; N 5.38; S 18.85 |
| I-35 | 86 | 158–61 | C 62.36; H 8.20; N 7.27; S 11.10 |
|  |  |  | C 62.33; H 8.18; N 7.22; S 11.16 |
| I-36 | 81 | 152–4 | C 63.65; H 8.18; N 6.96; S 10.62 |
|  |  |  | C 63.62; H 8.11; N 6.91; S 10.60 |
| I-37 | 79 | 176–8 | C 62.17; H 7.37; N 8.53; S 9.76 |
|  |  |  | C 62.13; H 7.29; N 8.54; S 9.79 |
| I-38 | 78 | 131–3 | C 60.25; H 8.06; N 6.59; S 15.08 |
|  |  |  | C 60.22; H 8.05; N 6.48; S 15.04 |
| I-39 | 81 | 84–6 | C 59.50; H 7.68; N 5.34; S 18.33 |
|  |  |  | C 59.51; H 7.66; N 5.27; S 18.23 |
| I-40 | 82 | 102–4 | C 60.79; H 8.19; N 6.44; S 14.75 |
|  |  |  | C 60.69; H 8.08; N 6.43; S 14.67 |
| I-41 | 86 | 135–7 | C 62.61; H 7.06; N 6.85; S 10.45 |
|  |  |  | C 62.62; H 7.02; N 6.82; S 10.51 |
| I-42 | 82 | 165–7 | C 62.36; H 8.20; N 7.27; S 11.10 |
|  |  |  | C 62.40; H 8.19; N 7.25; S 11.09 |

In the above tables;
Compd.: Compound
Noncry.: Noncrystalline

EXAMPLE 2

(Effect 1 as photographic additive)

Preparation of Sample 101:

A sample 101 of a multilayer color photographic light-sensitive material having the layers of the following compositions on a triacetyl cellulose film support of 127 μm in thickness having a subbing layer was prepared. The numerals each shows the addition amount per m$^2$. In addition, the effects of the compounds added are not limited to the use as described below.

| Layer 1: | Antihalation layer | | |
|---|---|---|---|
| | Black colloid silver | Ag amount | 0.30 g |
| | Gelatin | | 2.20 g |
| | Ultraviolet absorbent U-1 | | 0.08 g |
| | Ultraviolet absorbent U-3 | | 0.04 g |
| | Ultraviolet absorbent U-4 | | 0.08 g |
| | High-boiling organic solvent Oil-1 | | 0.11 g |
| | Fine crystal solid dispersion of Dye E-1 | | 0.25 g |
| | Fine crystal solid dispersion of dye E-2 | | 0.10 g |
| Layer 2: | Interlayer | | |
| | Gelatin | | 0.50 g |
| | Compound Cpd-A | | 5.0 mg |
| | Compound Cpd-E | | 1.0 mg |
| | High-boiling organic solvent Oil-3 | | 0.10 g |
| | Dye D-5 | | 4.0 mg |
| | Dye D-6 | | 3.0 mg |
| Layer 3: | Interlayer | | |
| | Yellow colloid silver | Ag amount | 0.010 g |
| | Gelatin | | 0.40 g |
| | Compound Cpd-I | | 20 mg |
| | High-boiling organic solvent Oil-3 | | 10 mg |
| Layer 4: | Low-sensitivity red-sensitive emulsion layer | | |
| | Emulsion A | Ag amount | 0.35 g |
| | Emulsion B | Ag amount | 0.15 g |
| | Gelatin | | 0.80 g |
| | Coupler C-1 | | 0.10 g |
| | Coupler C-2 | | 0.04 g |
| | Coupler C-6 | | 0.06 g |
| | Coupler C-12 | | 0.05 g |
| | Compound Cpd-A | | 5.0 mg |
| | High-boiling organic solvent Oil-2 | | 0.10 g |
| Layer 5: | Intermediate-sensitivity red-sensitive emulsion layer | | |
| | Emulsion B | Ag amount | 0.22 g |
| | Emulsion C | Ag amount | 0.30 g |
| | Gelatin | | 0.80 g |
| | Coupler C-1 | | 0.13 g |
| | Coupler C-2 | | 0.06 g |
| | Coupler C-6 | | 0.01 g |
| | Coupler C-12 | | 0.05 g |
| | High-boiling organic solvent Oil-2 | | 0.10 g |
| Layer 6: | High-sensitivity red-sensitive emulsion layer | | |
| | Emulsion D | Ag amount | 0.40 g |
| | Gelatin | | 1.70 g |
| | Coupler C-3 | | 0.70 g |
| | Coupler C-6 | | 0.02 g |
| | Additive P-1 | | 0.20 g |
| | High-boiling organic solvent Oil-2 | | 0.04 g |
| Layer 7: | Interlayer | | |
| | Gelatin | | 0.90 g |
| | Compound M-1 | | 0.20 g |
| | Compound Cpd-D | | 0.04 g |
| | Compound Cpd-G | | 0.16 g |
| | Compound Cpd-J | | 20 mg |
| Layer 8: | Interlayer | | |
| | Gelatin | | 1.10 g |
| | Compound Cpd-A | | 0.10 g |
| | Compound Cpd-B | | 0.10 g |
| | Compound Cpd-C | | 0.17 g |
| | Compound Cpd-I | | 50 mg |
| | High-boiling organic solvent Oil-4 | | 40 mg |
| | High-boiling organic solvent Oil-3 | | 0.15 g |
| Layer 9: | Low-sensitivity green-sensitive emulsion layer | | |
| | Emulsion E | Ag amount | 0.10 g |
| | Emulsion F | Ag amount | 0.20 g |
| | Emulsion G | Ag amount | 0.20 g |
| | Gelatin | | 0.50 g |
| | Coupler C-7 | | 0.03 g |
| | Coupler C-8 | | 0.09 g |
| | Coupler C-10 | | 0.04 g |
| | Coupler C-11 | | 0.04 g |
| | Compound Cpd-A | | 0.01 g |
| | Compound Cpd-F | | 0.3 mg |
| | High-boiling organic solvent Oil-2 | | 0.10 g |
| Layer 10: | Intermediate-sensitivity green-sensitive emulsion layer | | |
| | Emulsion G | Ag amount | 0.30 g |
| | Emulsion H | Ag amount | 0.10 g |
| | Gelatin | | 0.50 g |
| | Coupler C-4 | | 0.12 g |
| | Coupler C-10 | | 0.06 g |
| | Coupler C-11 | | 0.06 g |
| | Compound Cpd-F | | 0.03 g |
| | High-boiling organic solvent Oil-2 | | 0.01 g |
| Layer 11: | High-sensitivity green-sensitive emulsion layer | | |
| | Emulsion I | Ag amount | 0.50 g |
| | Gelatin | | 0.50 g |
| | Coupler C-4 | | 0.18 g |
| | Coupler C-10 | | 0.09 g |
| | Coupler C-11 | | 0.09 g |
| | Compound Cpd-F | | 0.08 g |
| | High-boiling organic solvent Oil-2 | | 0.020 g |
| Layer 12: | Interlayer | | |
| | Gelatin | | 0.30 g |
| Layer 13: | Yellow filter layer | | |
| | Yellow colloid silver | Ag amount | 0.01 g |
| | Fine crystal solid dispersion of dye E-3 | | 0.25 g |
| | Gelatin | | 0.50 g |
| | Compound Cpd-B | | 0.02 g |
| | Compound Cpd-D | | 0.03 g |
| | Compound Cpd-G | | 0.10 g |
| Layer 14: | Low-sensitivity blue-sensitive emulsion layer | | |
| | Emulsion J | Ag amount | 0.20 g |
| | Emulsion K | Ag amount | 0.30 g |
| | Gelatin | | 0.80 g |
| | Coupler C-5 | | 0.30 g |
| | Coupler C-6 | | 5.0 mg |
| | Coupler C-9 | | 0.03 g |
| Layer 15: | Intermediate-sensitivity blue-sensitive emulsion layer | | |
| | Emulsion L | Ag amount | 0.30 g |
| | Emulsion M | Ag amount | 0.30 g |
| | Gelatin | | 0.60 g |
| | Coupler C-5 | | 0.30 g |
| | Coupler C-6 | | 5.0 mg |
| | Coupler C-9 | | 0.03 g |
| Layer 16: | High-sensitivity blue-sensitive emulsion layer | | |
| | Emulsion N | Ag amount | 0.20 g |
| | Emulsion O | Ag amount | 0.20 g |
| | Gelatin | | 2.60 g |
| | Coupler C-5 | | 0.10 g |
| | Coupler C-6 | | 0.10 g |
| | Coupler C-9 | | 1.00 g |
| | Compound Cpd-E | | 10 mg |
| | High-boiling organic solvent Oil-2 | | 0.40 g |
| Layer 17: | 1st Protective layer | | |
| | Gelatin | | 1.10 g |
| | Ultraviolet absorbent U-1 | | 0.08 g |
| | Ultraviolet absorbent U-2 | | 0.03 g |
| | Ultraviolet absorbent U-5 | | 0.15 g |
| | Dye D-1 | | 0.03 g |
| | Dye D-2 | | 0.050 g |
| | Dye D-3 | | 0.10 g |
| | Dye D-4 | | 0.03 g |

-continued

| | | | |
|---|---|---|---|
| | Compound Cpd-H | | 0.40 g |
| | Compound Cpd-K | | 20 mg |
| | High-boiling organic solvent Oil-2 | | 0.30 g |
| Layer 18: | 2nd Protective layer | | |
| | Yellow colloid silver | Ag amount | 0.10 mg |
| | Fine-grain silver iodobromide emulsion (average grain diameter 0.06 μm, AgI content 1 mol %) | Ag amount | 0.10 g |
| | Gelatin | | 0.70 g |
| | Ultraviolet absorbent U-1 | | 0.06 g |
| | Ultraviolet absorbent U-2 | | 0.02 g |
| | Ultraviolet absorbent U-5 | | 0.10 g |
| | High-boiling organic solvent Oil-2 | | 0.07 g |
| Layer 19: | 3rd Protective layer | | |
| | Gelatin | | 1.40 g |
| | Polymethyl methacrylate (average particle diameter 1.5 μm) | | 5.0 mg |
| | Copolymer of methyl methacrylate and methacrylic acid at 6:4 (average particle diameter 1.5 μm) | | 0.10 g |
| | Cpd-S | | 0.030 g |

The light-sensitive silver halide emulsions used for the color photographic light-sensitive material are shown in Tables 4, 5 and 6 below.

TABLE 4

| Emulsion name | Feature of grain | Average grain diameter*1 (μm) | V.E*2 (%) | AgI*3 (%) |
|---|---|---|---|---|
| A | mono-14 | 0.28 | 16 | 4.0 |
| B | mono-cube | 0.30 | 10 | 4.0 |
| C | mono-cube | 0.38 | 10 | 5.0 |
| D | mono-tab-3 | 0.68 | 8 | 2.0 |
| E | mono-cube | 0.20 | 17 | 4.0 |
| F | mono-14 | 0.25 | 16 | 4.0 |
| G | mono-cube | 0.40 | 11 | 4.0 |
| H | mono-cube | 0.50 | 9 | 3.5 |
| I | mono-tab-5 | 0.80 | 10 | 2.0 |
| J | mono-cube | 0.30 | 18 | 4.0 |
| K | mono-14 | 0.45 | 17 | 4.0 |
| L | mono-tab-5 | 0.55 | 10 | 2.0 |
| M | mono-tab-8 | 0.70 | 13 | 2.0 |
| N | mono-tab-6 | 1.00 | 10 | 1.5 |
| O | mono-tab-9 | 1.20 | 15 | 1.5 |

In the above table;

*1: Equivalent-sphere average grain diameter

*2: Coefficient of variation

*3: Content of AgI mono-14: Monodisperse tetradecahedral grains mono-cube: Monodisperse cubic grains Mono-tab-3: Monodisperse tabular grains having average aspect ratio of 3.0

Mono-tab-5: Monodisperse tabular grains having average aspect ratio of 5.0

Mono-tab-8: Monodisperse tabular grains having average aspect ratio of 8.0

Mono-tab-6: Monodisperse tabular grains having average aspect ratio of 6.0

Mono-tab-9: Monodisperse tabular grains having average aspect ratio of 9.0

TABLE 5

| Emulsion name | Sensitizing dye added | Addition amount per mol of silver halide (g) |
|---|---|---|
| A | S-2 | 0.025 |
| | S-3 | 0.25 |
| | S-8 | 0.010 |
| B | S-1 | 0.010 |
| | S-3 | 0.25 |
| | S-8 | 0.010 |
| C | S-1 | 0.010 |
| | S-2 | 0.010 |
| | S-3 | 0.25 |
| | S-8 | 0.010 |
| D | S-2 | 0.010 |
| | S-3 | 0.10 |
| | S-8 | 0.010 |
| E | S-4 | 0.50 |
| | S-5 | 0.10 |
| | S-12 | 0.10 |
| F | S-4 | 0.30 |
| | S-5 | 0.10 |
| | S-12 | 0.10 |
| G | S-4 | 0.25 |
| | S-9 | 0.05 |
| | S-12 | 0.050 |
| H | S-4 | 0.20 |
| | S-5 | 0.060 |
| | S-9 | 0.050 |
| I | S-4 | 0.30 |
| | S-5 | 0.070 |
| | S-9 | 0.10 |
| | S-12 | 0.050 |

TABLE 6

| Emulsion name | Sensitizing dye added | Addition amount per mol of silver halide (g) |
|---|---|---|
| J | S-6 | 0.050 |
| | S-7 | 0.10 |
| | S-10 | 0.050 |
| | S-11 | 0.050 |
| K | S-6 | 0.05 |
| | S-7 | 0.10 |
| | S-10 | 0.030 |
| | S-11 | 0.030 |
| L | S-6 | 0.060 |
| | S-7 | 0.22 |
| M | S-6 | 0.050 |
| | S-7 | 0.17 |
| N | S-6 | 0.040 |
| | S-7 | 0.15 |
| O | S-6 | 0.060 |
| | S-7 | 0.12 |
| | S-10 | 0.050 |
| | S-11 | 0.050 |

Also, in addition to the above-described components, additives F-1 to F-9, surface active agents W-1 to W-7, and a gelatin hardening agent H-1 were further added.

Furthermore, as antiseptics and antifungal agents, phenol, 1,2-benzisothiazolin-3-on, 2-phenoxy ethanol, phenethyl alcohol, and p-benzoic acid ethyl ester were added.

The swelling ratio (the ratio of the swelled layer thickness to the dry layer thickness) of the sample 101 was 1.8.

The compounds used for preparing the sample are shown below.

C-1
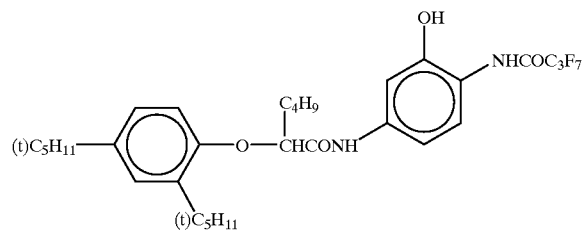
C-2
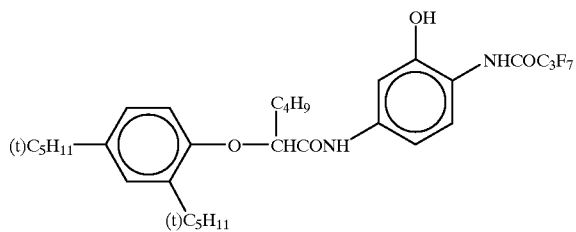
C-3
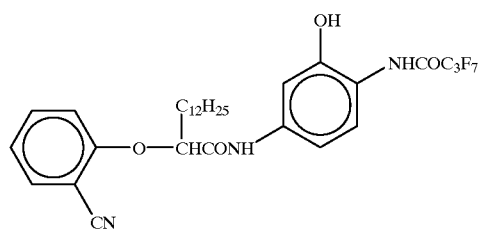
C-4
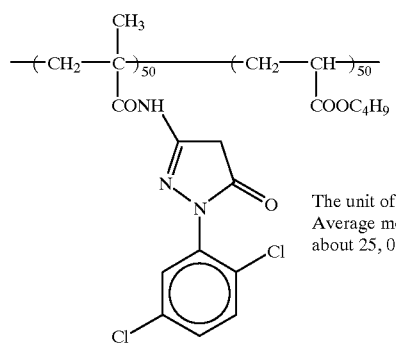
The unit of the numeral is wt%.
Average molecular weight: about 25,000
C-5
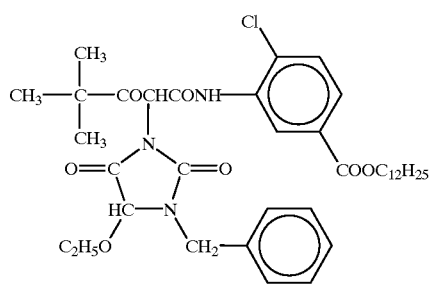
C-6
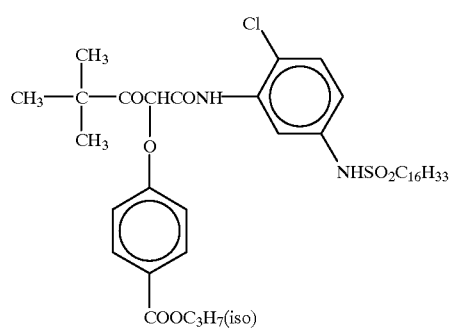
C-7
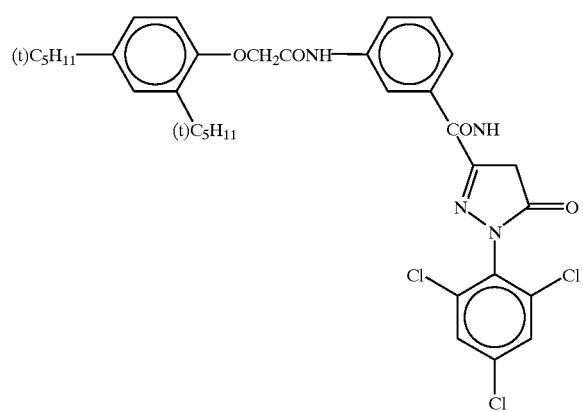
C-8
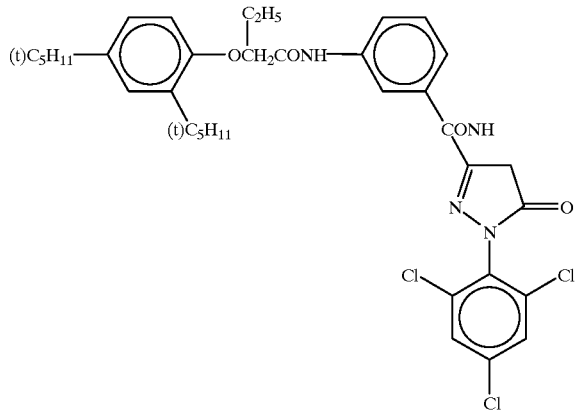

-continued
C-9
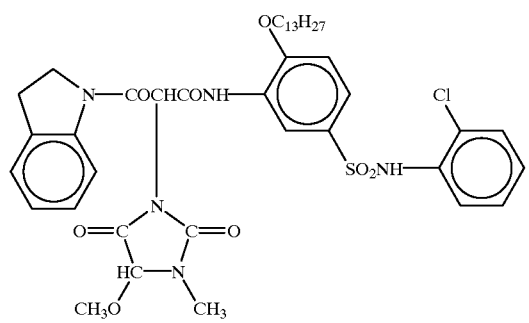
Oil-1
Dibutyl Phthalate
Oil-2
Tricresyl Phosphate
Oil-3
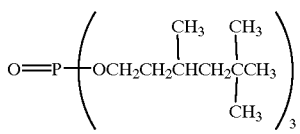
Oil-4
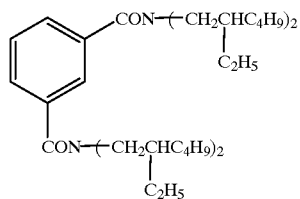
C-10
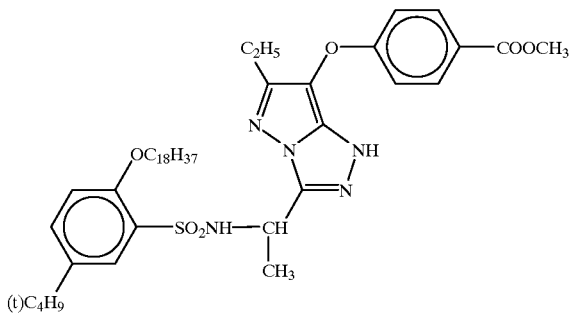
C-11
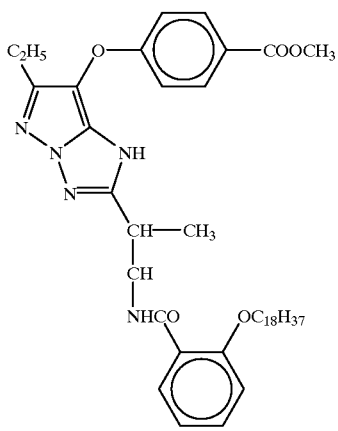
C-12
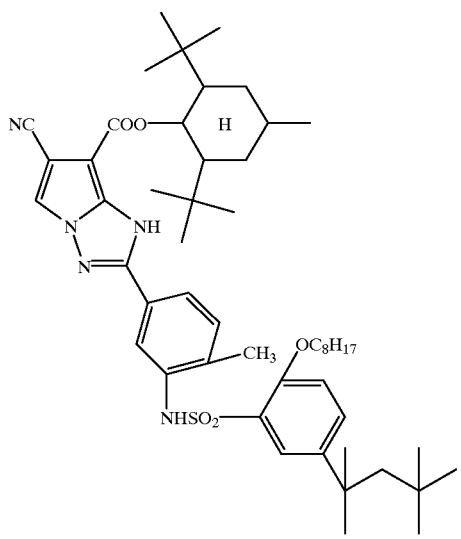
U-1
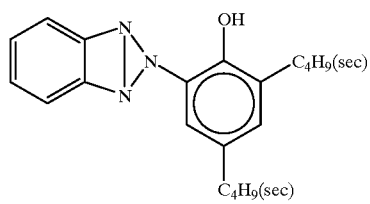
U-2
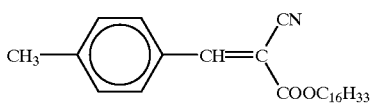

-continued
U-3 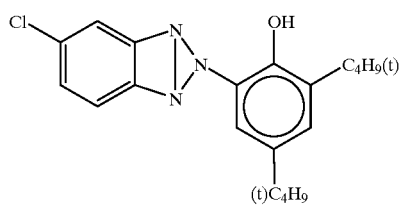 U-4 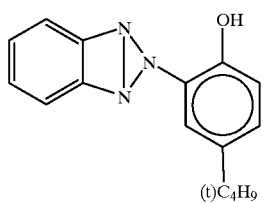
U-5 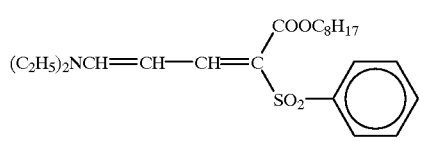 U-6 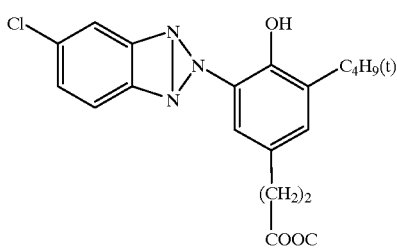
Cpd-A 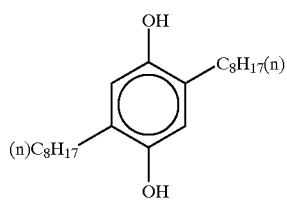 Cpd-B 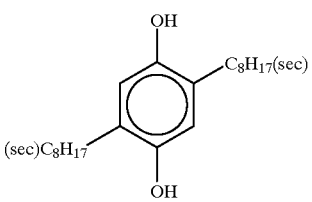
Cpd-C 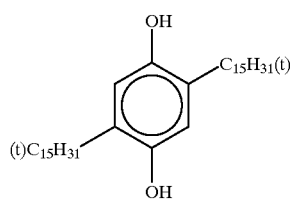 Cpd-D 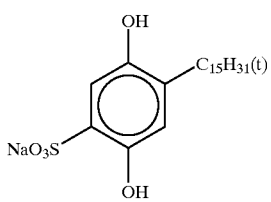
Cpd-E 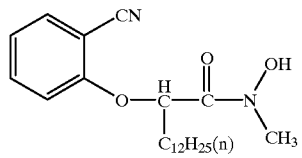 Cpd-F 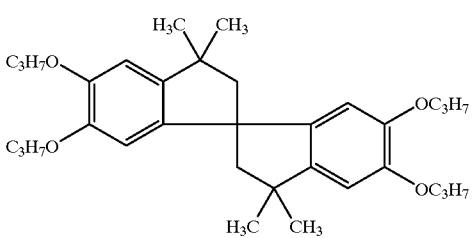
Cpd-G
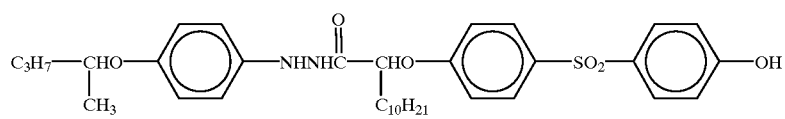
Cpd-H 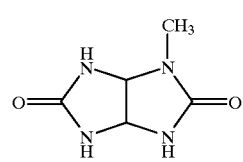 Cpd-S 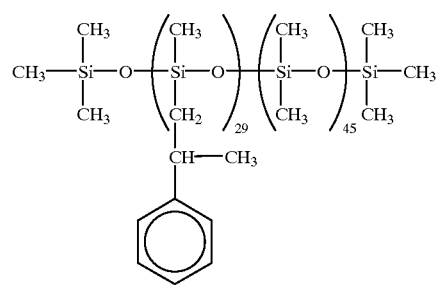

-continued
Cpd-I
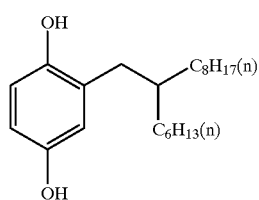
Cpd-J
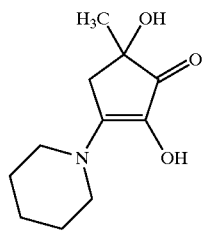
Cpd-K
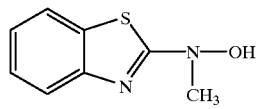
D-1
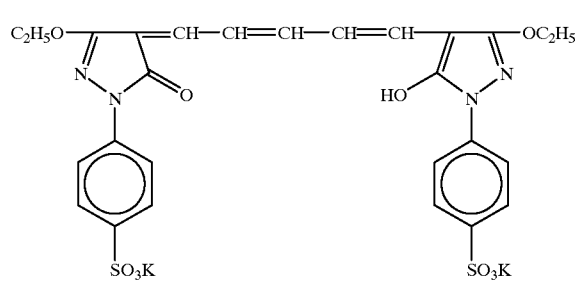
D-2
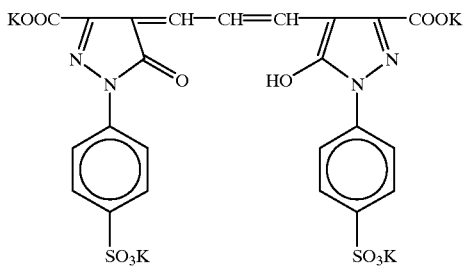
D-3
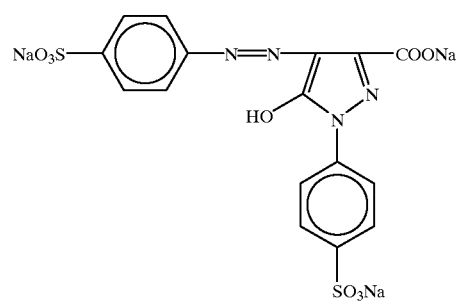
D-4
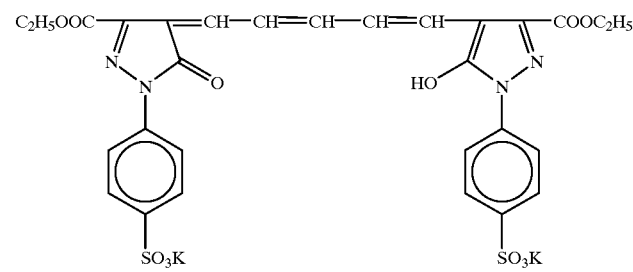
D-5
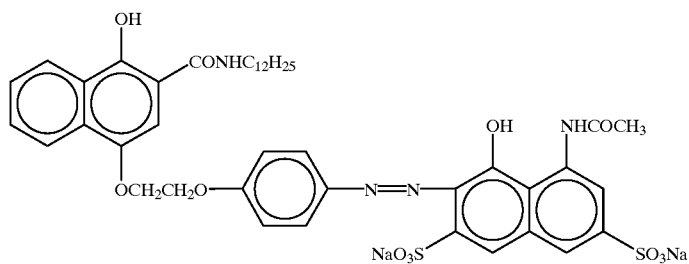

-continued
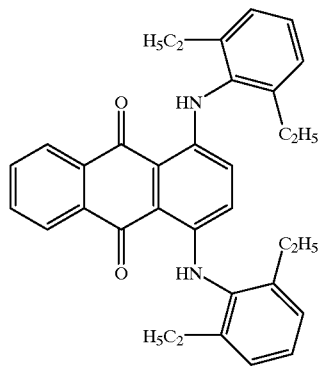
D-6
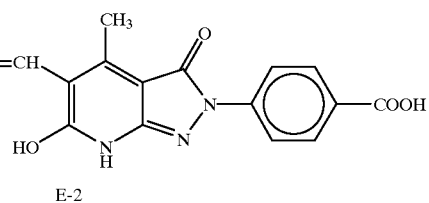
E-1
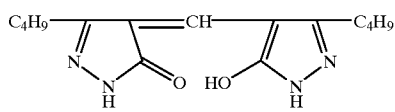
E-2
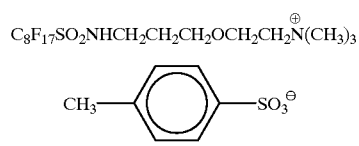
E-3
COOH
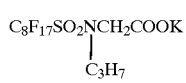
H-1
$C_8F_{17}SO_2NHCH_2CH_2CH_2OCH_2CH_2\overset{\oplus}{N}(CH_3)_3$    W-1
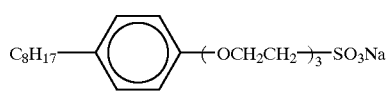
$C_8F_{17}SO_2NCH_2COOK$
   |
   $C_3H_7$
W-2
$NaO_3S-\overset{CH_2COOCH_2CH(C_2H_5)C_4H_9}{\underset{}{CHCOOCH_2CH(C_2H_5)C_4H_9}}$
W-3
$C_8H_{17}$—⟨phenyl⟩—$(OCH_2CH_2)_3$—$SO_3Na$
W-4
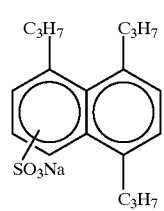
W-5
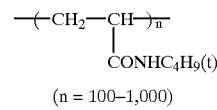
W-6
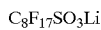
$C_8F_{17}SO_3Li$
W-7
$\underset{\underset{(n = 100-1,000)}{}}{-(CH_2-CH)_n-\underset{CONHC_4H_9(t)}{|}}$
P-1

-continued

-continued

S-5
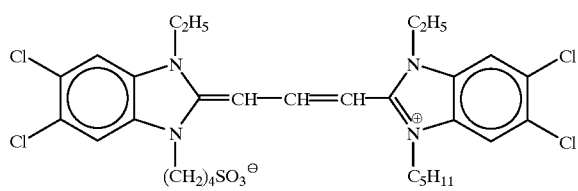

S-6
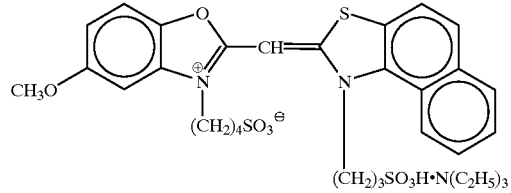

S-7
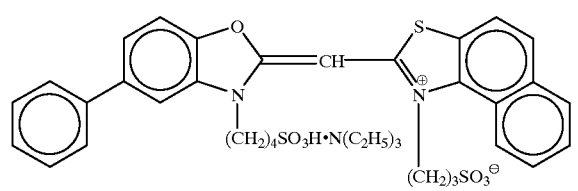

S-8
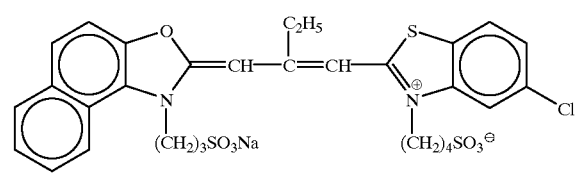

S-9
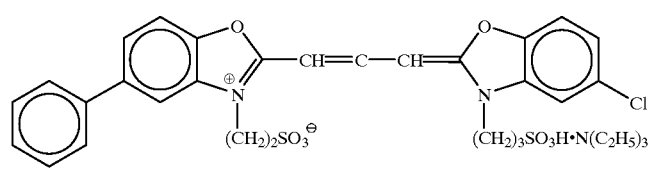

S-10
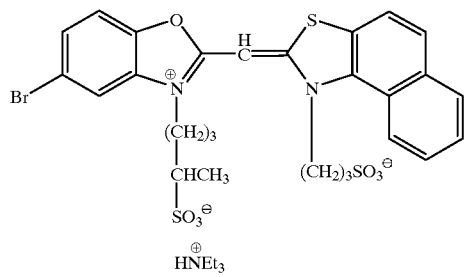

S-11
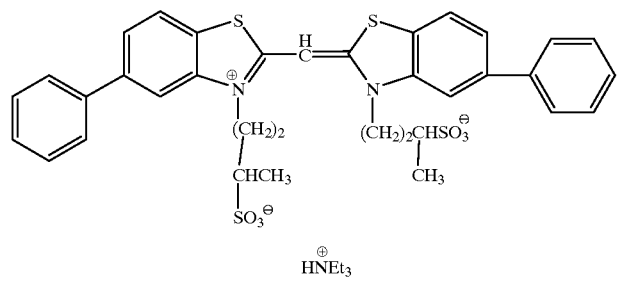

S-12

Preparation of the dispersion of organic solid disperse dye:

The dye E-1 was dispersed by the following method. That is, water and 200 g of Pluronic F88 (ethylene oxidepropylene oxide block copolymer) made by BASF A.G. were added to 1430 g of a wett cake of a dye containing 30% of methanol followed by stirring to form a slurry having a dye concentration of 6%. Then, in a ultraviscomill (UVM-2) (trade name, manufactured by Aimex Co.) were filled 1700 ml of zirconia beads having an average particle diameter of 0.5 mm and the above-described slurry was passed therethrough and ground for 8 hours at the circumference speed of about 10 meters/second and at a jetting amount of 0.5 liter/minute. The beads were removed by filtration and after adding water to the filtrate to dilute at a dye concentration of 3%, the filtrate was heated for 10 hours at 90° C. for the stabilization. The average particle diameter of the fine dye particles obtained was 0.60 μm and the distribution width of the particle diameters (particle diameter standard deviation× 100/average particle diameter) was 18%.

Similarly, the solid dispersions of the dye E-2 and the dye E-3 respectively were obtained. The average particle diameters of the fine dye particles were 0.54 μm and 0.56 μm respectively.

Preparation of Samples 102 to 118:

By following the same procedure as preparing the Sample 101 except that Comparative compound A was added to the layers 3, 4, 10, 16, and 18 of the Sample 101 at the coated amounts (overages) of $8\times10^{-4}$ mmol, $5\times10^{-3}$ mmol, $1\times10^{-3}$ mmol, $3\times10^{-3}$ mmol, and $6\times10^{-3}$ mmol respectively, Sample 102 was prepared.

Also, by following the same procedure of preparing the Sample 102 except that the Comparative compound A used in the Sample 102 was replaced with the equimolar amount of Comparative compound B, Comparative compound C, compounds I-1, I-2, I-7, I-8, I-9, I-12, I-13, I-17, I-25, I-26, I-27, I-29, I-35, and I-36 respectively, Samples 103 to 118 were prepared.

The comparative compounds used for preparing the above-described comparative samples are shown below.

Comparative Compound A:

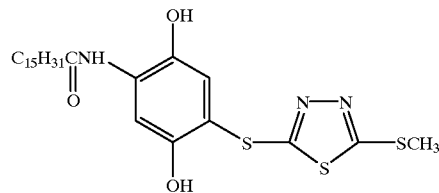

(the compound described in JP-A-3-226745)

Comparative Compound B:

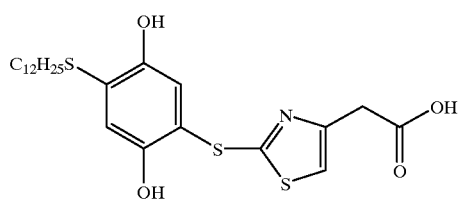

(the compound described in U.S. Pat. No. 5,380,633)

Comparative Compound C:

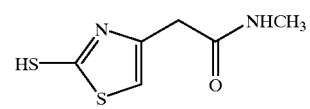

(the compound released from the compounds I-1, I-2, I-12, etc., of the present invention)

Comparative Compounds A, B and C and the compounds of the present invention each was dissolved in four times of tricyclohexyl phosphate, two times of high-boiling organic solvent Oil-3, four times of ethyl acetate, 0.1 times of di-t-octylhydroquinone and two times of U-6, as much as the weight of the compound, under heating. An oily phase component on the solution was added to eight times of aqueous phase component (having a gelatin concentration of 10%, and containing surface active agents W-5 and W-3 each at a concentration of 0.1%) as much as the weight of the oily phase component and the mixture was stirred with maintaining the mixture at a temperature of 50° C. to obtain an emulsified dispersion. The dispersion was added to each layer.

Evaluation of samples:

After exposing each of the samples 101 to 118 to while light through a continuous wedge, the sample was subjected to the photographic processing described below and image densities obtained were measured. The sensitivities were obtained from the reciprocals of the exposure amounts giving the density of 1.0 about the cyan, magenta, and yellow color image densities of each sample as relative sensitivities to those of the sample 101 taken as 100, respectively and shown as the red sensitivity (S(R)), the green sensitivity (S(G)), and the blue sensitivity (S(B)).

Then, each of the samples 101 to 118 was exposed to a red light of the same exposure amount as the red light exposure amount at the above-described white light exposure through the same continuous wedge as the white light exposure and subjected to the photographic processing described below. the difference in the logarithmic values of the exposure amounts [ΔlogE(R)] in the cyan density of 1.0 at the white light exposure and the red light exposure was determined, which was defined as the measure for the interimage effect for the red-sensitive emulsion layer. Similarly, the measures ΔlogE(G) and ΔlogE(B) of the interimage effect for the green-sensitive emulsion layer and the blue-sensitive emulsion layer were determined.

Furthermore, each of the samples 101 to 118 was exposed to a white light through a MTF pattern and subjected to the photographic processing described below. Also, the comparison of the sharpness was performed at the value of MTF of 10 cycles/mm.

The summaries of the samples prepared as described above and the evaluation results thereof are shown in Table 7 below.

TABLE 7

| Sample No. | Added Compound | Relative Sensitivity | | | Interimage Effect | | | MTF Value | | |
|---|---|---|---|---|---|---|---|---|---|---|
| | | S (R) | S (G) | S (B) | ΔlogE (R) | ΔlogE (G) | ΔlogE (B) | Cyan | Magenta | Yellow |
| 101 | none | 100 | 100 | 100 | 0.08 | 0.07 | 0.06 | 0.72 | 0.79 | 0.85 |
| 102 | A*1 | 100 | 98 | 100 | 0.14 | 0.06 | 0.06 | 0.75 | 0.80 | 0.84 |
| 103 | B*2 | 100 | 98 | 98 | 0.08 | 0.08 | 0.07 | 0.78 | 0.79 | 0.82 |
| 104 | C*3 | 94 | 96 | 96 | 0.20 | 0.08 | 0.07 | 0.73 | 0.79 | 0.82 |
| 105 | I-1 | 102 | 102 | 100 | 0.29 | 0.15 | 0.13 | 0.84 | 0.87 | 0.94 |
| 106 | I-2 | 106 | 101 | 100 | 0.29 | 0.14 | 0.14 | 0.83 | 0.90 | 0.91 |
| 107 | I-7 | 105 | 100 | 98 | 0.28 | 0.13 | 0.12 | 0.85 | 0.87 | 0.93 |
| 108 | I-8 | 104 | 100 | 99 | 0.28 | 0.14 | 0.14 | 0.87 | 0.90 | 0.94 |
| 109 | I-9 | 105 | 103 | 104 | 0.27 | 0.12 | 0.12 | 0.86 | 0.89 | 0.93 |

TABLE 7-continued

| Sample No. | Added Compound | Relative Sensitivity S (R) | S (G) | S (B) | Interimage Effect ΔlogE (R) | ΔlogE (G) | ΔlogE (B) | MTF Value Cyan | Magenta | Yellow |
|---|---|---|---|---|---|---|---|---|---|---|
| 110 | I-12 | 101 | 99 | 101 | 0.26 | 0.11 | 0.14 | 0.86 | 0.93 | 0.95 |
| 111 | I-13 | 98 | 102 | 100 | 0.27 | 0.11 | 0.13 | 0.83 | 0.86 | 0.93 |
| 112 | I-17 | 102 | 98 | 100 | 0.26 | 0.12 | 0.12 | 0.84 | 0.89 | 0.92 |
| 113 | I-25 | 105 | 102 | 102 | 0.29 | 0.14 | 0.12 | 0.85 | 0.85 | 0.93 |
| 114 | I-26 | 103 | 101 | 100 | 0.28 | 0.13 | 0.14 | 0.86 | 0.89 | 0.92 |
| 115 | I-27 | 104 | 103 | 103 | 0.25 | 0.12 | 0.12 | 0.90 | 0.90 | 0.89 |
| 116 | I-29 | 100 | 99 | 100 | 0.26 | 0.12 | 0.13 | 0.85 | 0.89 | 0.92 |
| 117 | I-35 | 104 | 102 | 100 | 0.29 | 0.15 | 0.14 | 0.84 | 0.87 | 0.92 |
| 118 | I-36 | 100 | 98 | 100 | 0.29 | 0.14 | 0.13 | 0.84 | 0.87 | 0.92 |

Note: In the above Table 7,

Sample Nos. 101 to 104: Samples for comparison

Sample Nos. 105 to 118: Samples of the present invention.

*1: Comparative Compound A

*2: Comparative Compound B

*3: Comparative Compound C

From the results of Table 7 above, it can be seen that in the comparative samples, the interimage effect is insufficient and the sensitivity is greatly lowered, on the other hand, the sample using the compounds of the present invention does not show undesirable lowering of the sensitivity, shows an improved interimage effect, and is excellent in the sharpness. Photographic processing:

| Process | Time (min.) | Temp. (° C.) | Tank volume (liter) | Replenishing amount (ml/m²) |
|---|---|---|---|---|
| 1st Development | 6 | 38 | 12 | 2200 |
| 1st Wash | 2 | 38 | 4 | 7500 |
| Reversal | 2 | 38 | 4 | 1100 |
| Color development | 6 | 38 | 12 | 2200 |
| Pre-bleach | 2 | 38 | 4 | 1100 |
| Bleach | 6 | 38 | 2 | 220 |
| Fix | 4 | 38 | 8 | 1100 |
| 2nd Wash | 4 | 38 | 8 | 7500 |
| Final rinse | 1 | 25 | 2 | 1100 |

The composition of each processing solution was as follows.

| 1st Developer | Tank | Replenisher |
|---|---|---|
| Nitrilo-N,N,N-trimethylenesulfonic acid.5-sodium salt | 1.5 g | 1.5 g |
| Diethylenetriaminepentaacetic acid.5-sodium salt | 2.0 g | 2.0 g |
| Sodium sulfite | 30 g | 30 g |
| Hydroquinone.potassium monosulfonate | 20 g | 20 g |
| Potassium carbonate | 15 g | 20 g |
| Sodium hydrogencarbonate | 12 g | 15 g |
| 1-Phenyl-4-methyl-4-hydroxymethyl-3-pyrazolidone | 1.5 g | 20. g |
| Potassium bromide | 2.5 g | 1.4 g |
| Potassium thiocyanate | 1.2 g | 1.2 g |
| Potassium iodide | 2.0 mg | — |
| Diethylene glycol | 13 g | 15 g |
| Water to make | 1000 ml | 1000 ml |
| pH | 9.60 | 9.60 |

The pH was adjusted with sulfuric acid or potassium hydroxide.

| Reversal Liquid | Tank | |
|---|---|---|
| Nitrilo-N,N,N-trimethylenephosphonic acid.5-sodium salt | 3.0 g | Replenisher is same as tank liquid. |
| Stannous chloride.5-hydrate | 1.0 g | |
| p-Aminophenol | 0.1 g | |
| Sodium hydroxide | 8 g | |
| Glacial acetic acid | 15 ml | |
| Water to make | 1000 ml | |
| pH | 6.00 | |

The pH was adjusted with acetic acid or sodium hydroxide.

| Color Developer | Tank | Replenisher |
|---|---|---|
| Nitrilo-N,N,N-trimethylenesulfonic acid.5-sodium salt | 2.0 g | 2.0 g |
| Sodium sulfite | 7.0 g | 7.0 g |
| Sodium tertiary phosphate.12-hydrate | 36 g | 36 g |
| Potassium bromide | 1.0 g | — |
| Potassium iodide | 90 mg | — |
| Sodium hydroxide | 3.0 g | 3.0 g |
| Citrazinic acid | 1.5 g | 1.5 g |
| N—Ethyl-N—(β-methanesulfonamidoethyl)-3-methyl-4-aminoaniline.3/2 sulfuric acid.monohydrate | 11 g | 11 g |
| 3,6-Dithiaoctane-1,8-diol | 1.0 g | 1.0 g |
| Water to make | 1000 ml | 1000 ml |
| pH | 11.80 | 12.00 |

The pH was adjusted with sulfuric acid or potassium hydroxide.

| Pre-bleach | Tank | Replenisher |
|---|---|---|
| Ethylenediaminetetraacetic acid.disodium salt.dihydrate | 8.0 g | 8.0 g |
| Sodium sulfite | 6.0 g | 8.0 g |
| 1-Thioglycerol | 0.4 g | 0.4 g |
| Formaldehyde-sodium hydrogensulfite addition product | 30 g | 35 g |
| Water to make | 1000 ml | 1000 ml |
| pH | 6.30 | 6.10 |

The pH was adjusted with acetic acid or sodium hydroxide.

| Bleach | Tank | Replenisher |
|---|---|---|
| Disodium ethylenediaminetetra-acetate.dihydrate | 2.0 g | 4.0 g |
| Ammonium ethylenediaminetetra-acetato ferrate.dihydrate | 120 g | 240 g |
| Potassium bromide | 100 g | 200 g |
| Ammonium nitrate | 10 g | 20 g |
| Water to make | 1000 ml | 1000 ml |
| pH | 5.70 | 5.50 |

The pH was adjusted with nitric acid or sodium hydroxide.

| Fix Liquid | Tank | |
|---|---|---|
| Ammonium thiosulfate | 80 g | Replenisher is |
| Sodium sulfite | 5.0 g | same as the |
| Sodium hydrogensulfite | 5.0 g | tank liquid. |
| Water to make | 1000 ml | |
| pH | 6.60 | |

The pH was adjusted with acetic acid or aqueous ammonia.

| Stabilization | Tank | Replenisher |
|---|---|---|
| 1,2-Benzoisothiazolin-3-on | 0.02 g | 0.03 g |
| Polyoxyethylene-p-monononylphenyl ether (average polymerization degree 10) | 0.3 g | 0.3 g |
| Polymaleic acid (average molecular weight 2,000) | 0.1 g | 0.15 g |
| Water to make | 1000 ml | 1000 ml |
| pH | 7.0 | 7.0 |

EXAMPLE 3
(Effect 2 as photographic additive)

1) Support

The support used in Example 3 of the present invention was prepared by the following method. 250° After drying a mixture of 100 parts by weight of polyethylene-2,6-naphthalate polymer and 2 parts by weight of an ultraviolet absorbent, Tinuvin P.326 (trade name, made by Ciba-Geigy Corporation), the mixture was melted at 300° C., extruded from a T-form die, subjected to a longitudinal stretch of 3.3 times at 140° C., then subjected to a width stretch of 3.3 times at 130° C., and further thermally fixed at 250° C. for 6 seconds to provide a PEN film of 90 μm in thickness. In addition, to the PEN film were added proper amounts of blue dyes, magenta dyes, and yellow dyes (I-1, I-4, I-6, I-24, I-26, I-27, and II-5 described in *JIII Journal of Technical Disclosure*, No. 94-6023). Furthermore, the PEN film was wound round a stainless steel-made winding core having a diameter of 20 cm and a thermal history of 48 hours at 110° C. was applied to provide a support which was hard to form curling by winding.

2) Coating of underlayer

After applying a corona discharging treatment, a UV irradiation treatment, and further a glow discharging treatment to both surfaces of the support, a coating composition for underlayer made up of 0.1 g/m² of gelatin, 0.01 g/m² of sodium α-sulfo-di-2-ethylhexylsuccinate, 0.04 g/m² of salicylic acid, 0.2 g/m² of p-chlorophenol, 0.012 g/m² of $(CH_2\!=\!CHSO_2CH_2CH_2NHCO)_2CH_2$, 0.02 g/m² of polyamido-epichlorohydrin polycondensation product, and water was coated on each surface (10 ml, using a bar coater) to form an underlayer. Drying was performed at 115° C. for 6 minutes by passing the coated support through a drying zone. (The rollers and the conveyers of the drying zone were all kept at 115° C.)

3) Formation of back layers

On one surface of the above-described support thus coated with the underlayers were coated an antistatic layer, a magnetic recording layer, and a lubricating layer each having the composition described below as back layers.

3-1) Formation of antistatic layer

An antistatic layer was formed on the surface of the underlayer formed on the surface of the support by coating a coating composition made up of 0.2 g/m² of a dispersion (secondary aggregated particle diameters of about 0.08 μm) of the fine particle powder of a tin oxide-antimony oxide composite having an average particle diameter of 0.005 μm and a specific resistance of 5 Ω·cm, 0.05 g/m² of gelatin, 0.02 g/m² of $(CH_2\!=\!CHSO_2CH_2CH_2NHCO)_2CH_2$, 0.005 g/m² of polyoxyethylene-p-nonylphenol (polymerization degree of 10), and 0.22 g/m² of resorcin.

3-2) Formation of magnetic recording layer

A coating composition made up of 0.06 g/m² of cobalt-γ-iron oxide (specific surface area 43 m²/g, long axis 0.14 μm, short axis 0.03 μm, saturation magnetization 89 emu/g, $Fe^{+2}/Fe^{+3}=6/94$, the surfaces were treated with aluminum oxide and silicon oxide of 2% by weight of the iron oxide) coated with 15% by weight 3-polyoxyethylenepropyloxytrimethoxysilane (polymerization degree 15), 1.2 g/m² of diacetyl cellulose (the dispersion of the iron oxide was carried out by an open kneader and a sand mill), 0.3 g/m² of $C_2H_5C(CH_2OCONHC_6H_3(CH_3)NCO)_3$ as a curing agent, and acetone, methyl ethyl ketone, and cyclohexanone as solvents was coated thereon by a bar coater to form a magnetic recording layer of 1.2 μm in thickness. Also, 10 mg/m² of silica particles (particle diameter 0.3 μm) and 10 mg/m² of aluminum oxide (particle diameter 0.15 μm) as abrasive coated with 15% by weight 3-polyoxyethylenepropyloxytrimethoxysilane (polymerization degree 15) were added to the magnetic recording layer as matting agents. Drying thereof was performed at 115° C. for 6 minutes (the rollers and the conveyer of the drying zone were all kept at 115° C.). The color density increase of DB of the magnetic recording layer with an X-Right (blue filter) was about 0.1, the saturated magnetic moment of the magnetic recording layer was 4.2 emu/g, the coercive force thereof was 7.3×10⁴ A/m. and the squareness ratio thereof was 65%.

3-3) Preparation of Lubricating layer

A mixture of 25 mg/M² of diacetyl cellulose, 6 mg/m² of $C_6H_{13}CH(OH)C_{10}H_{20}COOC_{40}H_8$, (Compound a), and 9 mg/M² of $C_{50}H_{101}O(CH_2CH_2O)_{16}H$ (Compound b) was coated. In addition, the mixture was molten in xylene/propylene monomethyl ether (1/1) at 105° C., the molten mixture was poured and dispersed in propylene monomethyl ether of a normal temperature in an amount of 10 times the amount of the molten mixture, and then after dispersing in acetone (average particle diameter 0.01 μm), the dispersion was added. Then, 15 mg/m² of silica particles (0.3 μm) as a matting agent and 15 mg/m² of aluminum oxide (0.15 μm) coated with 15% by weight 3-polyoxyethylenepropyloxytrimethoxysilane (polymerization degree 15) as an abrasive were added to the layer. Drying was performed at 115° C. for 6 minutes (the rollers and the conveyer in the drying zone were all kept at 115° C.). The lubricating layer had excellent characteristics that the kinematic friction coefficient was 0.06 (stainless steel hard ball of 5 mm in diameter, load 100 g, and speed 6 cm/minute), the static friction coefficient was 0.07 (clip method) or the kinetic a C-friction coefficient of the lubricating layer and the emulsion surface described below was also 0.12.

By following the same procedure as Example 2 except the above-described support was used in place of the supports for Samples 101 to 118 of Example 2, Samples 201 to 218 were prepared and evaluated. The results obtained were almost same as the results in Example 2.

As described above, according to the present invention, the novel compound for photography is provided and by using the compound the silver halide-color photographic material having the improved interimage effect and the improved sharpness can be provided.

While the invention has been described in detail and with reference to specific embodiments thereof, it will be apparent to one skilled in the art that various changes and modifications can be made therein without departing from the spirit and scope thereof.

What is claimed is:

1. A compound represented by following formula (I):

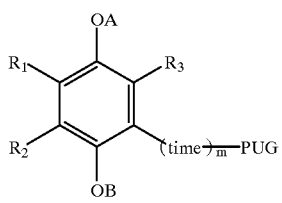

(I)

wherein $R_1$ represents an alkyl group, an alkylthio group, an acylamino group, or a ureido group; $R_2$ and $R_3$ each represents a hydrogen atom or a group capable of being substituted; A and B each represents a hydrogen atom or a group which can be removed with an alkali; —(time)$_m$—PUG is released from an oxidation product of the compound of formula (I), and "time" represents a group releasing PUG after —(time)$_m$— PUG is released from an oxidation product of the compound of formula (I); m represents 0 or 1; and PUG represents a group represented by following formula (II):

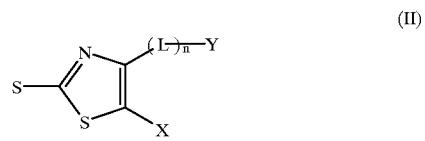

(II)

wherein n represents 1; L represents a methylene group, an ethylene group, or a propylene group; Y represents a hydrogen atom, a carbamoyl group, or an alkoxycarbonyl group; and X represents a hydrogen atom, a methyl group, an ethyl group, a carboxyl group, an alkoxycarbonyl group, a cyano group, or a carbamoyl group.

2. The compound for photography as claimed in claim 1 wherein in the formula (I), $R_1$ represents an alkylthio group, an acylamino group, or a ureido group and in the formula (II), n represents 1; L represents a methylene group; Y represents a hydrogen atom, a carbamoyl group, or an alkoxycarbonyl group; and X represents a hydrogen atom.

3. The compound for photography as claimed in claim 2 wherein in the formula (II), Y represents a carbamoyl group.

4. The compound for photography as claimed in claim 2 wherein in the formula (II), Y represents —C(=O)NHCH$_3$, —C(=O)NHC$_2$H$_5$, —C(=O)NHC$_3$H$_7$, or —C(=O)NHCH(CH$_3$)$_2$.

* * * * *